United States Patent [19]

Friesen et al.

[11] Patent Number: 5,576,338
[45] Date of Patent: Nov. 19, 1996

[54] BIS (BIARYL) COMPOUNDS AS INHIBITORS OF LEUKOTRIENE BIOSYNTHESIS

[75] Inventors: Richard Friesen, Dollard des Ormeaux; Yves Ducharme, Montreal; Daniel Dube', St. Lazare; Carole Lepine, Laval; Daniel Delorme, St. Lazare; Pierre Hamel, Laval, all of Canada

[73] Assignee: Merck Frosst Canada, Inc., Kirkland, Canada

[21] Appl. No.: 388,787

[22] Filed: Feb. 15, 1995

[51] Int. Cl.$^6$ .............. A61K 31/44; C07C 311/02; C07D 401/04

[52] U.S. Cl. .............. 514/337; 514/365; 514/374; 514/422; 514/444; 546/283.1; 548/203; 548/235; 548/562; 549/60; 549/283

[58] Field of Search .............. 549/283, 60; 514/457, 514/337, 365, 374, 422, 444; 546/283.1; 548/203, 235, 562

[56] References Cited

U.S. PATENT DOCUMENTS 5,424,320  6/1995  Fortin et al. .............. 514/337

FOREIGN PATENT DOCUMENTS 0385662  9/1990  European Pat. Off. .
0579304  1/1994  European Pat. Off. .
WO95/0330  2/1995  WIPO .
WO95/03309  2/1995  WIPO .

OTHER PUBLICATIONS

J. Med. Chem., 35:2600–2609 (1992).

*Primary Examiner*—Zinna Northington Davis
*Attorney, Agent, or Firm*—Mollie M. Yang; David L. Rose

[57] ABSTRACT

Compounds having the Formula I:

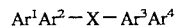

$$Ar^1Ar^2-X-Ar^3Ar^4 \qquad I$$

are inhibitors of leukotriene biosynthesis. These compounds are useful as anti-asthmatic, anti-allergic, anti-inflammatory, and cytoprotective agents. They are also useful in treating angina, cerebral spasm, glomerular nephritis, hepatitis, endotoxemia, uveitis, and allograft rejection and in preventing the formation of atherosclerotic plaques.

12 Claims, No Drawings

BIS (BIARYL) COMPOUNDS AS INHIBITORS OF LEUKOTRIENE BIOSYNTHESIS

BACKGROUND OF THE INVENTION

The leukotrienes constitute a group of locally acting hormones, produced in living systems from arachidonic acid. The major leukotrienes are Leukotriene $B_4$ (abbreviated as $LTB_4$), $LTC_4$, $LTD_4$ and $LTE_4$. The biosynthesis of these leukotrienes begins with the action of the enzyme 5-lipoxygenase on arachidonic acid to produce the epoxide known as Leukotriene $A_4$ ($LTA_4$), which is converted to the other leukotrienes by subsequent enzymatic steps. Further details of the biosynthesis as well as the metabolism of the leukotrienes are to be found in the book *Leukotrienes and Lipoxygenases*, ed. J. Rokach, Elsevier, Amsterdam (1989). The actions of the leukotrienes in living systems and their contribution to various diseases states are also discussed in the book by Rokach.

EP 385,662 (published Sep. 5, 1990) discloses 5-lipoxygenase inhibitors of the formula

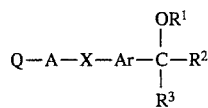

in which a heterocyclic moiety, Q, is linked to Ar, which may be phenylene, via A—X. The group attached to Ar represents a tertiary alcohol substituted O-, S- or N-containing heterocyclic ring, whereas the corresponding moiety in the present invention is a aromatic group. The $Ar^4$ unit of the present invention is absent from the above formula.

WO94/00444 (published Jan. 6, 1994) discloses leukotriene biosynthesis inhibitors which are aryl substituted naphthalenes of the formula

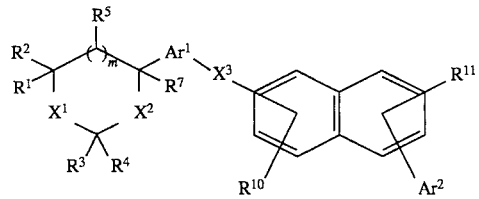

The present compounds differ from those of the above formula in that instead of the ring containing $X^1$ and $X^2$, they possess an aromatic ring.

Crawley et al., (*J. Med. Chem.*, 1992, 35, 2600–2609) discloses the 5-lipoxygenase inhibitor of the formula below. The compounds of the present invention differ in that they lack the tetrahydropyran ring, and that they possess an aromatic substituent on both the monocyclic and bicyclic ring moieties.

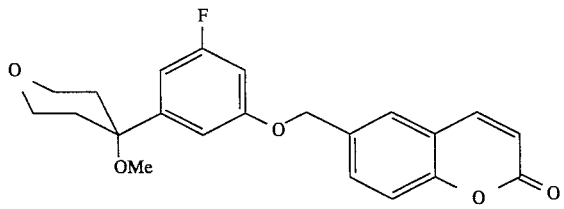

SUMMARY OF THE INVENTION

The present invention relates to bis(biaryl) compounds having activity as leukotriene biosynthesis inhibitors, to methods for their preparation, and to methods and pharmaceutical formulations for using these compounds in mammals (especially humans).

Because of their activity as leukotriene biosynthesis inhibitors, the compounds of the present invention are useful as anti-asthmatic, anti-allergic, anti-inflammatory, and cytoprotective agents. They are also useful in treating angina, cerebral spasm, glomerular nephritis, hepatitis, endotoxemia, uveitis, and allograft rejection and in preventing the formation of atherosclerotic plaques.

DETAILED DESCRIPTION OF THE INVENTION

The compounds of the present invention may be represented by the following Formula I:

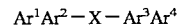

wherein:
  $Ar^1$ and $Ar^4$ are independently aryl-$(R^1)_2$, wherein aryl is a 5-membered aromatic containing one O or S and 0–3 N; a 5-membered aromatic ring containing 1–4 N; or a 6-membered aromatic ring containing 0–3 N;
  $Ar^2$ is arylene-$(R^2)_2$; wherein arylene is a 6-membered aromatic ring containing 0–3 N;
  $Ar^3$ is arylene-$(R^3)_2$, wherein arylene is a 10-membered bicyclic aromatic ring containing 0–3 N, 2H-1-benzopyran-2-one, or 2H-2-thioxo-1-benzopyran;
  X is $OCH_2$, $CH_2O$, O, S, S(O) or $S(O)_2$;
  $R_1$ is H, lower alkyl, lower alkoxy, lower alkylthio, lower alkylsulfinyl, lower alkylsulfonyl, CN, $CF_3$, $CO_2R^4$, or halogen;
  $R^2$ is H, lower alkyl, lower alkoxy, lower alkylthio, CN, $CF_3$ or halogen;
  $R^3$ is H, lower alkyl, lower alkoxy, lower alkylthio, lower alkylsulfinyl, lower alkylsulfonyl, CN, $CF_3$, $CO_2R^4$, or halogen;
  $R^4$ is H, or lower alkyl;
or a pharmaceutically acceptable salt thereof.

A preferred embodiment of the present invention is represented by Formula I:

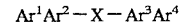

wherein:
  $Ar^1$ is Ph, Py, Fu, Th or Tz;
  $Ar^2$ is Phe, or Pye;
  $Ar^3$ is naphthalene, 2H-1-benzopyran-2-one, quinoline, or isoquinoline;
  $Ar^4$ is Ph, Py, Fu, Ox, or Pyr;
  X is $OCH_2$, $CH_2O$, S, S(O), or $S(O)_2$.

Definitions

The following abbreviations have the indicated meanings:

| | | |
|---|---|---|
| Ac | = | acetyl |
| AIBN | = | 2,2-azobisisobutyronitrile |
| $Bu_4NF$ | = | n-tetrabutylammonium fluoride |
| DDQ | = | 2,3-dichloro-5,6-dicyano-1,4-benzoquinone |
| DMAP | = | 4-(dimethylamino)pyridine |
| DMF | = | N,N-dimethylformamide |
| DMSO | = | dimethyl sulfoxide |
| $Et_3N$ | = | triethylamine |
| Fu | = | 2- or 3-furyl |
| mCPBA | = | meta-chloroperoxybenzoic acid |
| NBS | = | N-bromosuccinimide |

Definitions

| | | |
|---|---|---|
| NMP | = | N-methyl-2-pyrrolidinone |
| NSAID | = | non-steroidal anti-inflammatory drug |
| Ox | = | 2-, 4- or 5-oxazolyl |
| Ph | = | phenyl |
| Phe | = | benzenediyl |
| Py | = | 2-, 3- or 4-pyridyl |
| Pye | = | pyridinediyl |
| Pyr | = | 2- or 3-pyrrolyl |
| r.t. | = | room temperature |
| rac. | = | racemic |
| Th | = | 2- or 3-thienyl |
| THF | = | tetrahydrofuran |
| Tz | = | 2-, 4- or 5-thiazolyl |

Alkyl group abbreviations

| | | |
|---|---|---|
| Me | = | methyl |
| Et | = | ethyl |
| n-Pr | = | normal propyl |
| i-Pr | = | isopropyl |
| n-Bu | = | normal butyl |
| i-Bu | = | isobutyl |
| s-Bu | = | secondary butyl |
| t-Bu | = | tertiary butyl |
| c-Pr | = | cyclopropyl |
| c-Bu | = | cyclobutyl |
| c-Pen | = | cyclopentyl |
| c-Hex | = | cyclohexyl |

Alkyl, means linear, branched and cyclic structures and combinations thereof.

"Lower alkyl" means alkyl groups of from 1 to 7 carbon atoms. Examples of lower alkyl groups include methyl, ethyl, propyl, isopropyl, butyl, s- and t-butyl, pentyl, hexyl, heptyl, cyclopropyl, cyclopentyl, cyclohexylmethyl and the like.

"Lower alkoxy" means alkoxy groups of from 1 to 7 carbon atoms of a straight, branched, or cyclic configuration. Examples of lower alkoxy groups include methoxy, ethoxy, propoxy, isopropoxy, cyclopropyloxy, cyclohexyloxy, and the like.

"Lower alkylthio" means alkylthio groups of from 1 to 7 carbon atoms of a straight, branched or cyclic configuration. Examples of lower alkylthio groups include methylthio, propylthio, isopropylthio, cycloheptylthio, etc. By way of illustration, the propylthio group signifies —SCH$_2$CH$_2$CH$_3$.

"Lower alkysulfinyl" means those alkylsulfinyl groups of from 1 to 7 carbon atoms of a straight, branched or cyclic configuration. Examples of lower alkylsulfinyl groups are methylsulfinyl, 2-butylsulfinyl, cyclohexylmethylsulfonyl, etc. By way of illustration the 2-butylsulfinyl group signifies —S(O)CH(CH$_3$)CH$_2$CH$_3$.

"Lower alkylsulfonyl" means those alkylsulfonyl groups of from 1 to 7 carbon atoms of a straight, branched or cyclic configuration. Examples of lower alkylsulfonyl groups are methylsulfonyl, 2-butylsulfonyl, cyclohexylmethylsulfonyl, etc. By way of illustration the 2-butylsulfonyl group signifies —S(O)$_2$CH(CH$_3$)CH$_2$CH$_3$.

Halogen includes F, Cl, Br, and I.

Examples of "6-membered aromatic ring containing 0–3 N" include benzene, pyridine, pyridazine, pyrimidine, pyrazine, 1,2,3-triazine, 1,2,4-triazine and 1,3,5-triazine.

Examples of "10-membered bicyclic aromatic ring containing 0–3 N" include naphthalene, quinoline, isoquinoline, cinnoline, quinazoline, quinoxaline, and naphthyridine.

Examples of "5-membered aromatic ring containing one O or S and 0–3 N" include furan, oxazole, isoxazole, 1,2,5-oxadiazole, 1,3,4-oxadiazole, thiophene, thiazole, isothiazole, 1,2,4-thiadiazole and 1,3,4-thiadiazole.

Examples of "5-membered aromatic ring containing 1–4 N" include pyrrole, pyrazole, imidazole, 1,2,3-triazole, 1,2,4-triazole and tetrazole.

Optical Isomers—Diastereomers—Geometric Isomers

Some of the compounds described herein contain one or more asymmetric centers and may thus give rise to diastereomers and optical isomers. The present invention is meant to comprehend such possible diastereomers as well as their racemic and resolved, enantiomerically pure forms and pharmaceutically acceptable salts thereof.

Salts

The pharmaceutical compositions of the present invention comprise a compound of Formula I as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that in the discussion of methods of treatment which follows, references to the compounds of Formula I are meant to also include the pharmaceutically acceptable salts.

Utilities

The ability of the compounds of Formula I to inhibit biosynthesis of the leukotrienes makes them useful for preventing or reversing the symptoms induced by the leukotrienes in a human subject. This inhibition of the mammalian biosynthesis of leukotrienes indicates that the compounds and pharmaceutical compositions thereof are useful to treat, prevent, or ameliorate in mammals and especially in humans: 1) pulmonary disorders including diseases such as asthma, chronic bronchitis, and related obstructive airway diseases, 2) allergies and allergic reactions such as allergic rhinitis, contact dermatitis, allergic conjunctivitis, and the like, 3) inflammation such as arthritis or inflammatory bowel disease, 4) pain, 5) skin disorders such as atopic eczema, and the like, 6) cardiovascular disorders such as angina, formation of atherosclerotic plaques, myocardial ischemia, hypertension, platelet aggregation and the like, 7) renal insufficiency arising from ischaemia induced by immunological or chemical (cyclosporin) etiology and 8) migraine or cluster headache, 9) ocular conditions such as uveitis, 10) hepatitis resulting from chemical, immunological or infectious stimuli, 11) trauma or shock states such as burn injuries, endotoxemia and the like, 12) allograft rejection, 13) prevention of side effects associated with therapeutic administration of cytokines such as Interleukin II and rumor necrosis factor, 14) chronic lung diseases such as cystic fibrosis, bronchitis and other small- and large-airway diseases, 15) cholecystitis, 16) multiple sclerosis, and 17) proliferation of myoblastic leukemia cells.

Thus, the compounds of the present invention may also be used to treat or prevent mammalian (especially, human) disease states such as erosive gastritis; erosive esophagitis; diarrhea; cerebral spasm; premature labor; spontaneous abortion; dysmenorrhea; ischemia; noxious agent-induced damage or necrosis of hepatic, pancreatic, renal, or myocardial tissue; liver parenchymal damage caused by hepatoxic agents such as $CCl_4$ and D-galactosamine; ischemic renal failure; disease-induced hepatic damage; bile salt induced pancreatic or gastric damage; trauma- or stress-induced cell damage; and glycerol-induced renal failure. The compounds also act as inhibitors of rumor metastasis and exhibit cytoprotective action.

The cytoprotective activity of a compound may be observed in both animals and man by noting the increased resistance of the gastrointestinal mucosa to the noxious effects of strong irritants, for example, the ulcerogenic effects of aspirin or indomethacin. In addition to lessening the effect of non-steroidal anti-inflammatory drugs on the gastrointestinal tract, animal studies show that cytoprotective compounds will prevent gastric lesions induced by oral administration of strong acids, strong bases, ethanol, hypertonic saline solutions, and the like.

Two assays can be used to measure cytoprotective ability. These assays are; (A) an ethanol-induced lesion assay and (B) an indomethacin-induced ulcer assay and are described in EP 140,684.

Dose Ranges

The magnitude of prophylactic or therapeutic dose of a compound of Formula I will, of course, vary with the nature of the severity of the condition to be treated and with the particular compound of Formula I and its route of administration. It will also vary according to the age, weight and response of the individual patient. In general, the daily dose range for anti-asthmatic, anti-allergic or anti-inflammatory use and generally, uses other than cytoprotection, lie within the range of from about 0.001 mg to about 100 mg per kg body weight of a mammal, preferably 0.01 mg to about 10 mg per kg, and most preferably 0.1 to 1 mg per kg, in single or divided doses. On the other hand, it may be necessary to use dosages outside these limits in some cases.

For use where a composition for intravenous administration is employed, a suitable dosage range for anti-asthmatic, anti-inflammatory, or anti-allergic use is from about 0.001 mg to about 25 mg (preferably from 0.01 mg to about 1 mg) of a compound of Formula I per kg of body weight per day and for cytoprotective use from about 0.1 mg to about 100 mg (preferably from about 1 mg to about 100 mg and more preferably from about 1 mg to about 10 mg) of a compound of Formula I per kg of body weight per day.

In the case where an oral composition is employed, a suitable dosage range for anti-asthmatic, anti-inflammatory or anti-allergic use is, e.g., from about 0.01 mg to about 100 mg of a compound of Formula I per kg of body weight per day, preferably from about 0.1 mg to about 10 mg per kg and for cytoprotective use from 0.1 mg to about 100 mg (preferably from about 1 mg to about 100 mg and more preferably from about 10 mg to about 100 mg) of a compound of Formula I per kg of body weight per day.

For the treatment of diseases of the eye, ophthalmic preparations for ocular administration comprising 0.001–1% by weight solutions or suspensions of the compounds of Formula I in an acceptable ophthalmic formulation may be used.

The exact amount of a compound of the Formula I to be used as a cytoprotective agent will depend on, inter alia, whether it is being administered to heal damaged cells or to avoid future damage, on the nature of the damaged cells (e.g., gastrointestinal ulcerations vs. nephrotic necrosis), and on the nature of the causative agent. An example of the use of a compound of the Formula I in avoiding future damage would be co-administration of a compound of the Formula I with an NSAID that might otherwise cause such damage (for example, indomethacin). For such use, the compound of Formula I is administered from 30 minutes prior up to 30 minutes after administration of the NSAID. Preferably it is administered prior to or simultaneously with the NSAID, (for example, in a combination dosage form).

Pharmaceutical Composition

Any suitable route of administration may be employed for providing a mammal, especially a human with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like.

The pharmaceutical compositions of the present invention comprise a compound of Formula I as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

For administration by inhalation, the compounds of the present invention are conveniently delivered in the form of an aerosol spray presentation from pressurized packs or nebulisers. The compounds may also be delivered as powders which may be formulated and the powder composition may be inhaled with the aid of an insufflation powder inhaler device. The preferred delivery system for inhalation is a metered dose inhalation (MDI) aerosol, which may be formulated as a suspension or solution of a compound of Formula I in suitable propellants, such as fluorocarbons or hydrocarbons.

Suitable topical formulations of a compound of Formula I include transdermal devices, aerosols, creams, ointments, lotions, dusting powders, and the like.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carriers are obviously employed. If desired, tablets may be coated by standard aqueous or nonaqueous techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200 and 4,008,719, the disclosures of which are hereby incorporated herein by reference.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from about 1 mg to about 500 mg of the active ingredient and each cachet or capsule contains from about 1 to about 500 mg of the active ingredient.

The following are examples of representative pharmaceutical dosage forms for the compounds of Formula I:

| Injectable Suspension (I.M.) | mg/ml |
|---|---|
| Compound of Formula I | 10 |
| Methylcellulose | 5.0 |
| Tween 80 | 0.5 |
| Benzyl alcohol | 9.0 |
| Benzalkonium chloride | 1.0 |
| Water for injection to a total volume of 1 mL | |

| Tablet | mg/tablet |
|---|---|
| Compound of Formula I | 25 |
| Microcrystalline Cellulose | 415 |
| Providone | 14.0 |
| Pregelatinized Starch | 43.5 |
| Magnesium Stearate | 2.5 |
| | 500 |

| Capsule | mg/capsule |
|---|---|
| Compound of Formula I | 25 |
| Lactose Powder | 573.5 |
| Magnesium Stearate | 1.5 |
| | 600 |

| Aerosol | Per canister |
|---|---|
| Compound of Formula I | 24 mg |
| Leciam, NF Liquid Concentrate | 1.2 mg |
| Trichlorofluoromethane, NF | 4.025 gm |
| Dichlorodifluoromethane, NF | 12.15 gm |

Combinations with Other Drugs

In addition to the compounds of Formula I, the pharmaceutical compositions of the present invention can also contain other active ingredients, such as cyclooxygenase inhibitors, non-steroidal anti-inflammatory drugs (NSAIDs), peripheral analgesic agents such as zomepirac diflunisal and the like. The weight ratio of the compound of the Formula I to the second active ingredient may be varied and will depend upon the effective dose of each ingredient. Generally, an effective dose of each will be used. Thus, for example, when a compound of the Formula I is combined with an NSAID the weight ratio of the compound of the Formula I to the NSAID will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

NSAIDs can be characterized into five groups:

(1) propionic acid derivatives;

(2) acetic acid derivatives;

(3) fenamic acid derivatives;

(4) oxicams; and (5) biphenylcarboxylic acid derivatives, or a pharmaceutically acceptable salt thereof.

The propionic acid derivatives which may be used comprise: alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, prano-profen, suprofen, tiaprofenic acid, and tioxaprofen. Structurally related propionic acid derivatives having similar analgesic and anti-inflammatory properties are also intended to be included in this group.

Thus, "propionic acid derivatives" as defined herein are non-narcotic analgesics/non-steroidal anti-inflammatory drugs having a free $-CH(CH_3)COOH$ or $-CH_2CH_2COOH$ group (which optionally can be in the form of a pharmaceutically acceptable salt group, e.g., $-CH(CH_3)COO^-Na^+$ or $-CH_2CH_2COO^-Na^+$), typically attached directly or via a carbonyl function to a ring system, preferably to an aromatic ring system.

The acetic acid derivatives which may be used comprise: indomethacin, which is a preferred NSAID, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac. Structurally related acetic acid derivatives having similar analgesic and anti-inflammatory properties are also intended to be encompassed by this group.

Thus, "acetic acid derivatives" as defined herein are non-narcotic analgesics/non-steroidal anti-inflammatory drugs having a free —CH₂COOH group (which optionally can be in the form of a pharmaceutically acceptable salt group, e.g., —CH₂COO⁻Na⁺), typically attached directly to a ring system, preferably to an aromatic or heteroaromatic ring system.

The fenamic acid derivatives which may be used comprise: flufenamic acid, meclofenamic acid, mefenamic acid, niflumic acid and tolfenamic acid. Structurally related fenamic acid derivatives having similar analgesic and anti-inflammatory properties are also intended to be encompassed by this group.

Thus, "fenamic acid derivatives" as defined herein are non-narcotic analgesics/non-steroidal anti-inflammatory drugs which contain the basic structure:

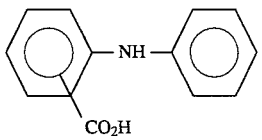

which can bear a variety of substituents and in which the free —COOH group can be in the form of a pharmaceutically acceptable salt group, e.g., —COO⁻Na⁺.

The biphenylcarboxylic acid derivatives which can be used comprise: diflunisal and flufenisal. Structurally related biphenylcarboxylic acid derivatives having similar analgesic and anti-inflammatory properties are also intended to be encompassed by this group.

Thus, "biphenylcarboxylic acid derivatives" as defined herein are non-narcotic analgesics/non-steroidal anti-inflammatory drugs which contain the basic structure:

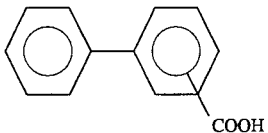

which can bear a variety of substituents and in which the free —COOH group can be in the form of a pharmaceutically acceptable salt group, e.g., —COO⁻Na⁺.

The oxicams which can be used in the present invention comprise: isoxicam, piroxicam, sudoxicam and tenoxican. Structurally related oxicams having similar analgesic and anti-inflammatory properties are also intended to be encompassed by this group.

Thus, "oxicams" as defined herein are non-narcotic analgesics/non-steroidal anti-inflammatory drugs which have the general formula:

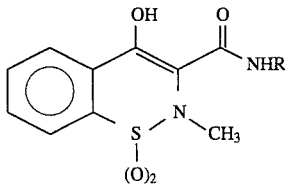

wherein R is an aryl or heteroaryl ring system.

The following NSAIDs may also be used: amfenac sodium, aminoprofen, anitrazafen, antrafenine, auranofin, bendazac lysinate, benzydanine, beprozin, broperamole, bufezolac, cinmetacin, ciproquazone, cloximate, dazidamine, deboxamet, delmetacin, detomidine, dexindoprofen, diacerein, di-fisalamine, difenpyramide, emorfazone, enfenamic acid, enolicam, epirizole, etersalate, etodolac, etofenamate, fanetizole mesylate, fenclorac, fendosal, fenflumizole, feprazone, floctafenine, flunixin, flunoxaprofen, fluproquazone, fopirtoline, fosfosal, furcloprofen, glucametacin, guaimesal, ibuproxam, isofezolac, isonixim, isoprofen, isoxicam, lefetamine HCl, leflunomide, lofemizole, lonazolac calcium, lotifazole, loxoprofen, lysin clonixinate, meclofenamate sodium, meseclazone, nabumetone, nictindole, nimesulide, orpanoxin, oxametacin, oxapadol, perisoxal citrate, pimeprofen, pimetacin, piproxen, pirazolac, pirfenidone, proglumetacin maleate, proquazone, pyridoxiprofen, sudoxicam, talmetacin, talniflumate, tenoxicam, thiazolinobutazone, thielavin B, tiaramide HCl, tiflamizole, timegadine, tolpadol, tryptamid, and ufenamate.

The following NSAIDs, designated by company code number (see e.g., Pharmaprojects), may also be used: 480156S, AA861, AD1590, AFP802, AFP860, AI77B, AP504, AU8001, BPPC, BW540C, CHINOIN 127, CN100, EB382, EL508, F1044, GV3658, ITF182, KCNTEI6090, KME4, LA2851, MR714, MR897, MY309, ONO3144, PR823, PV102, PV108, R830, RS2131, SCR152, SH440, SIR133, SPAS510, SQ27239, ST281, SY6001, TA60, TAI-901 (4-benzoyl-1-indancarboxylic acid), TVX2706, U60257, UR2301, and WY41770.

Finally, NSAIDs which may also be used include the salicylates, specifically acetyl salicylic acid and the phenylbutazones, and pharmaceutically acceptable salts thereof.

In addition to indomethacin, other preferred NSAIDs are acetyl salicylic acid, diclofenac, fenbufen, fenoprofen, flurbiprofen, ibuprofen, ketoprofen, naproxen, phenylbutazone, piroxicam, sulindac, and tolmetin. Pharmaceutical compositions comprising the Formula I compounds may also contain inhibitors of the biosynthesis of the leukotrienes such as are disclosed in EP 138,481 (Apr. 24, 1985), EP 115,394 (Aug. 8, 1984), EP 136,893 (Apr. 10, 1985), and EP 140,709 (May 8, 1985), which are hereby incorporated herein by reference.

The compounds of the Formula I may also be used in combination with leukotriene antagonists such as those disclosed in EP 106,565 (Apr. 25, 1984) and EP 104,885 (Apr. 4, 1984) which are hereby incorporated herein by reference and others known in the art such as those disclosed in EP Application Nos. 56,172 (Jul. 21, 1982) and 61,800 (Jun. 10, 1982); and in U.K. Patent Specification No. 2,058,785 (Apr. 15, 1981), which are hereby incorporated herein by reference.

Pharmaceutical compositions comprising the Formula I compounds may also contain as the second active ingredient, prostaglandin antagonists such as those disclosed in EP 11,067 (May 28, 1980) or thromboxane antagonists such as those disclosed in U.S. Pat. No. 4,237,160. They may also contain histidine decarboxylase inhibitors such as a-fluoromethylhistidine, described in U.S. Pat. No. 4,325,961. The compounds of the Formula I may also be advantageously combined with an H¹ or H²-receptor antagonist, such as, for instance, acetamazole, aminothiadiazoles disclosed in EP 40,696 (Dec. 2, 1981), benadryl, cimetidine, famotidine, framamine, histadyl, phenergan, ranitidine, terfenadine and like compounds, such as those disclosed in U.S. Pat. Nos. 4,283,408; 4,362,736; and 4,394,508. The pharmaceutical compositions may also contain a K⁺/H⁺ ATPase inhibitor such as omeprazole, disclosed in U.S. Pat. No. 4,255,431, and the like. Compounds of Formula I may also be usefully combined with most cell stabilizing agents, such as 1,3-bis(2-carboxychromon-5-yloxy)-2-hydroxypropane and related compounds described in British Patent Specifications 1,144,905 and 1,144,906. Another useful pharmaceutical composition comprises the Formula I compounds in combination with serotonin antagonists such as methysergide, the serotonin antagonists described in *Nature*, 316, 126–131 (1985), and the like. Each of the references referred to in this paragraph is hereby incorporated herein by reference.

Other advantageous pharmaceutical compositions comprise the Formula I compounds in combination with anticholinergics such as ipratropium bromide, bronchodilators such as the beta agonist salbutamol, metaproterenol, terbutaline, fenoterol and the like, and the anti-asthmatic drugs theophylline, choline theophyllinate and enprofylline, the calcium antagonists nifedipine, diltiazem, nitrendipine, verapamil, nimodipine, felodipine, etc. and the corticosteroids, hydrocortisone, methylprednisolone, betamethasone, dexamethasone, beclomethasone, and the like.

Methods of Synthesis

Compounds of Formula I of the present invention may be prepared according to the synthetic routes outlined in Schemes 1 to 6 and by following the methods described herein.

Scheme I

The quinoline 1A of Scheme 1 may be prepared in a multi-step sequence from an appropriately dihalogenated quinoline II. The quinoline II is firstly converted into the quinoline III by a regioselective reaction with an appropriate metalated aromatic in the presence of a catalyst such as tetrakis (triphenylphosphine) palladium. The conversion to the quinoline IV is achieved by treatment of III with a metalated methyl reagent in the presence of a catalyst such as [1,3-bis(diphenylphosphino)propane]nickel(II) chloride. The quinoline IV is converted into the quinoline V by first treatment with an oxidizing reagent such as m-chloroperoxybenzoic acid in an organic solvent followed by reaction of the intermediate N-oxide with an acylating reagent such as dialkylcarbamyl chloride, and a cyanating agent such as trimethylsilyl cyanide. Bromination of V is achieved upon treatment with a bromine source, such as N-bromosuccinimide and light. Coupling of the benzylic halide VI with the appropriate aromatic alcohol VII in an organic solvent such as DMF using an inorganic base such as $Cs_2CO_3$ provides compounds of Formula 1A of the present invention.

Scheme 2

The naphthalene 1B of the present invention may be prepared according to Scheme 2 by coupling of naphthol IX (WO 94/00444) and an appropriate arylmethyl alcohol VIII in an organic solvent such as THF by treatment with a phosphine and dialkyl azodicarboxylate, (the Mitsunobu reaction).

Scheme 3

The naphthalene 1C of Scheme 3 may be prepared in a multi-step sequence, from naphthalene IX (WO 94/00444). The naphthol IX is converted to the triflate X by treatment with a triflating agent such as triflic anhydride in the presence of a base such as pyridine in an organic solvent such as $CH_2Cl_2$. Conversion to the stannane XI is accomplished by treatment of X with a distannane in the presence of a transition metal catalyst such as $Pd(Ph_3P)_4$ in an organic solvent such as dioxane. The stannane XI is then converted into the iodide XII upon treatment with iodine in an organic solvent such as chloroform. The iodide XII is converted into the thiol XIII by a two-step procedure involving treatment of XII with a thiol such as 2-trimethylsilylethanethiol in the presence of a catalyst such as $Pd(Ph_3P)_4$ in an organic solvent such as ethanol, followed by deprotection with a fluoride source such as tetrabutylammonium fluoride. Coupling of the thiol XIII and the appropriate aryl halide XIV in an organic solvent such as NMP in the presence of a base such as $K_2CO_3$ provides compounds of Formula 1C of the present invention.

Scheme 4

The isoquinoline 1D of Scheme 4 may be prepared in a multi-step sequence from an appropriately substituted anisole XV. The amine XV is converted into the sulfonamide XVI by a two-step procedure involving sulfonylation using a sulfonylating agent such as p-toluenesulfonyl chloride in the presence of a base such as pyridine, followed by alkylation with an appropriate haloalkyl aryl ketone in the presence of a base such as $Cs_2CO_3$ in an organic solvent such as acetone. The cyclization of the sulfonamide XVI to provide XVII is achieved by heating in an acid such as trifluoroacetic acid. The demethylation of isoquinoline XVII is achieved under acidic conditions, such as heating with pyridine hydrochloride, leading to XVIII. The phenol XVIII is then converted into the iodide XIX by procedures similar to those described for the conversion of IX to XII in Scheme 3. Coupling of the iodide XIX and the appropriate aryl thiol XX in an organic solvent such as butanol in the presence of a base such as potassium t-butoxide and a catalyst such as $Pd(Ph_3P)_4$ provides compounds of Formula 1D of the present invention.

Scheme 5

Compounds of Formula 1E can be synthesized using the routes given in Scheme 5. Bromophenol XXI can be acetylated by treating a mixture of XXI and acetyl chloride in the presence of a base such as pyridine in a solvent such as dichloromethane to yield the corresponding acetate which, upon heating with a Lewis acid such as aluminum chloride, gives the acyl derivative XXII. Reaction of XXII with, first an inorganic base such as sodium hydride in an organic solvent such as benzene, followed by addition of a carbonate such as diethylcarbonate furnished the intermediate XXIII. The intermediate XXIII was then transformed using trifluoromethane-sulfonic anhydride, in the presence of an amine such as triethylamine, in a neutral solvent such as dichloromethane, to the corresponding triflate XXIV. Cross coupling of this material with an aryl lithium species (resulting from reaction of an aryl halide (Br or I) with an alkyl lithium such as n-BuLi in a mixture of THF/hexane), in the presence of trimethyl borate and catalyzed by a Pd(0) species such as $(Ph_3P)_4Pd$, in a mixture of THF and $H_2O$ as solvent, affords derivatives XXV. Compounds of Formula 1E can be obtained by heating a mixture of XXV and a thiol of general structure XX in a polar solvent such as NMP with an inorganic base like potassium carbonate.

Alternatively, the aromatic bromide XXV can be reacted by heating in the presence of trimethylsilylethane thiol and an inorganic base such as potassium carbonate in a polar solvent such as NMP to afford derivative XXVI. The thiol derivatives XXVII can be obtained by treating XXVI with $Bu_4NF$ in an organic solvent such as DMF. Sulfur linked compounds may be obtained by heating thiol XXVII with an aromatic halide of general Formula XIV in the presence of an inorganic base such as potassium carbonate in a polar solvent such as NMP to yield compounds of Formula 1E. Compounds of Formula 1F can be obtained by treating compounds of general structure 1E in the presence of a peracid such as metachloroperbenzoic acid in an organic solvent such as dichloromethane.

Scheme 6

Compounds of Formula 1G can be synthesized using the same protocol to obtain XXV (Scheme 5) except that compound XXI is replaced by metacresol XXVIII giving compound XXIX. Intermediate XXIX is then brominated by heating in the presence of a brominating reagent such as NBS in an organic solvent such as carbon tetrachloride in the presence of a catalytic amount of a radical initiator such as AIBN, giving access to compounds XXX. Bromide displacement can be accomplished using an aromatic alcohol of a general Structure VII in the presence of an inorganic base such as cesium carbonate in an aprotic dipolar solvent such as DMF to afford compounds of Formula 1G.

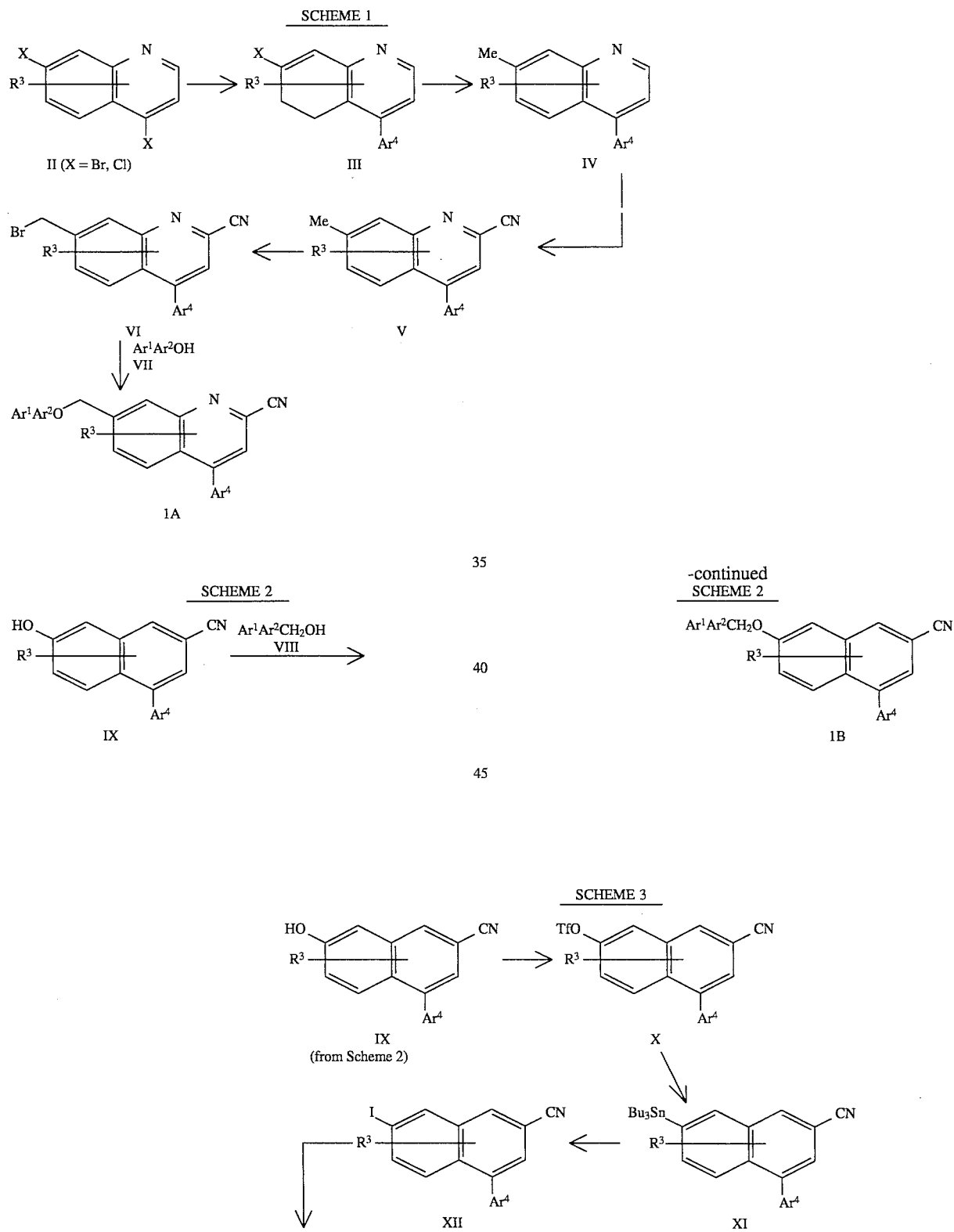

-continued
SCHEME 3
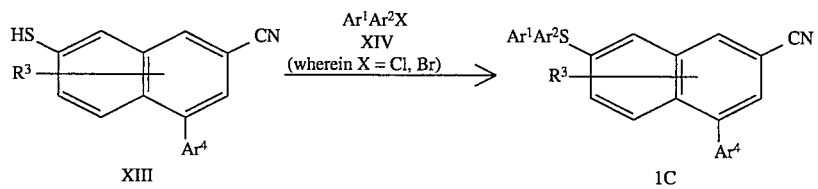
SCHEME 4
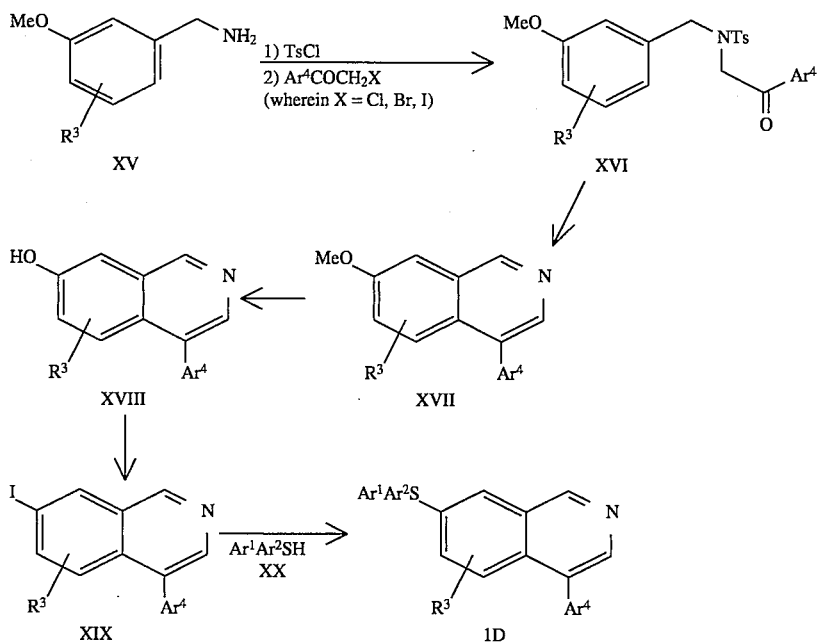
SCHEME 5
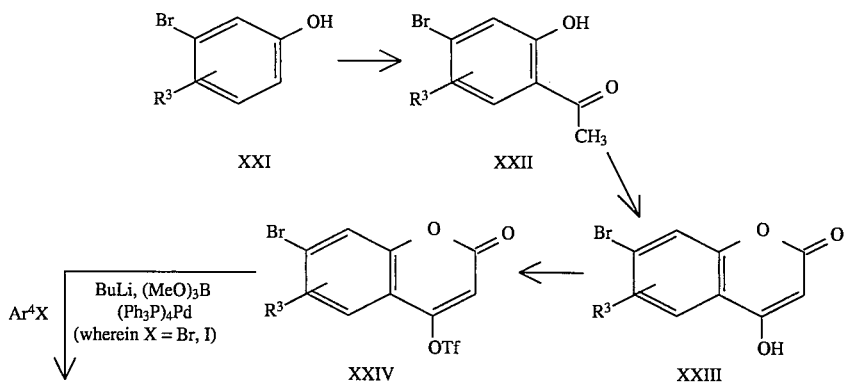

-continued
SCHEME 5
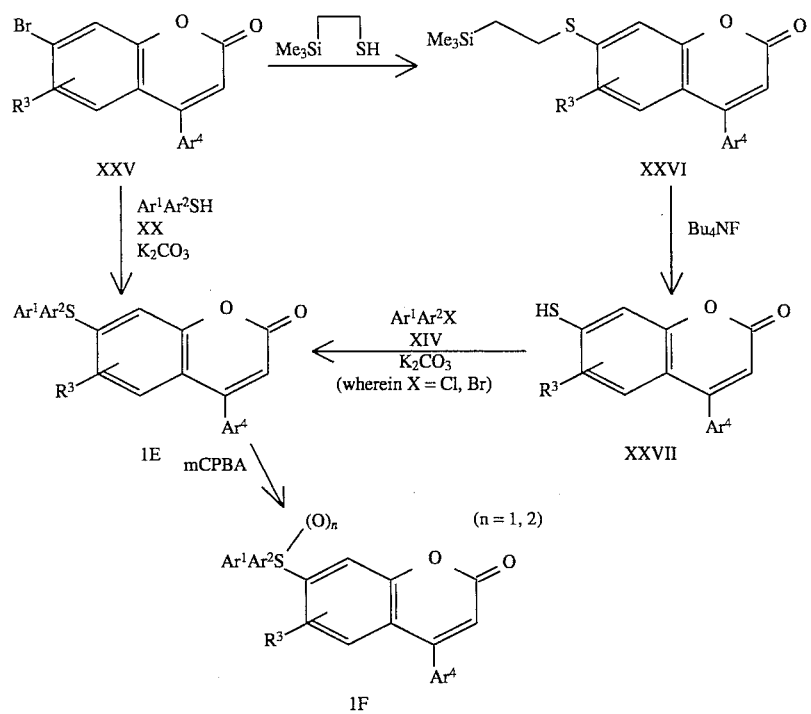
SCHEME 6
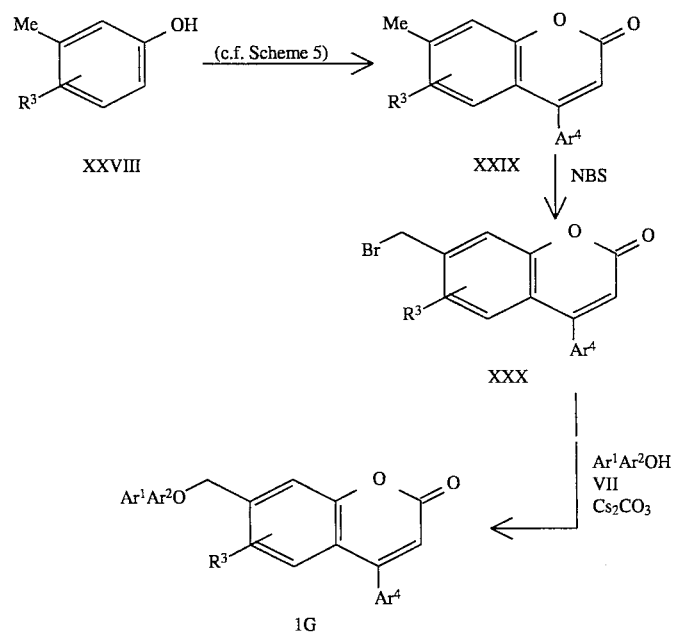

Representative Compounds

Tables 1–3 illustrate compounds of Formula I, which are representative of the present invention.

TABLE 1

Ar$^1$—Ar$^2$—OCH$_2$— [quinoline with CN and furan-O substituents]

| Ex | Ar$^1$ | Ar$^2$ |
|---|---|---|
| 1 | 4-Py | 5-(3-F-Phe) |
| 2 | Ph | 5-(3-F-Phe) |
| 3 | 2-OMe—Ph | 5-(3-F-Phe) |
| 4 | 3-Fu | 5-(3-F-Phe) |
| 5 | Ph | 4-Phe |
| 6 | 4-F—Ph | 5-(3-F-Phe) |
| 7 | 2-Py | 5-(3-F-Phe) |
| 8 | 3,5-diF—Ph | 5-(3-F-Phe) |
| 9 | 2-CO$_2$Me—Ph | 5-(3-F-Phe) |
| 10 | 2,4-diCl—Ph | 5-(3-F-Phe) |
| 11 | 2-SMe—Ph | 5-(3-F-Phe) |
| 12 | 2-SO$_2$Me—Ph | 5-(3-F-Phe) |
| 13 | 2-Tz | 5-(3-F-Phe) |
| 14 | 3-Py | 5-(3-F-Phe) |
| 15 | 2-Th | 5-(3-F-Phe) |

TABLE 2

Ar$^1$—Ar$^2$—X— [coumarin-type ring with Ar$^4$]

| Ex | Ar$^1$ | Ar$^2$ | X | Ar$^4$ |
|---|---|---|---|---|
| 16 | Ph | 5-(3-F—Phe) | OCH$_2$ | 3-Fu |
| 17 | Ph | 5-(3-F—Phe) | S | 3-Fu |
| 18 | Ph | 5-(3-F—Phe) | OCH$_2$ | Ph |
| 19 | Ph | 5-(3-F—Phe) | S(O) | 3-Fu |
| 20 | Ph | 5-(3-F—Phe) | S(O)$_2$ | 3-Fu |
| 21 | 3-Py | 5-(3-F—Phe) | S | 3-Fu |
| 22 | Ph | 6,2-Pye | S | 3-Fu |
| 23 | Ph | 5-(3-F—Phe) | S | 3-Py |
| 24 | 4-F—Ph | 5-(3-F—Phe) | S | 3-Fu |
| 25 | Ph | 5-(3-F—Phe) | S | 4-F—Ph |
| 26 | Ph | 5-(3-F—Phe) | S | 3-Pyr |
| 27 | 4-F—Ph | 5-(3-F—Phe) | S | 4-Ox |
| 28 | 4-F—Ph | 5-(3-F—Phe) | S | 3-Py |

TABLE 3

Ar$^1$—Ar$^2$—X— [naphthalene with CN and furan-O]

| Ex | Ar$^1$ | Ar$^2$ | X |
|---|---|---|---|
| 29 | Ph | 6,2-Pye | CH$_2$O |
| 30 | 4-Cl—Ph | 6,2-Pye | CH$_2$O |
| 31 | 4-F—Ph | 6,2-Pye | CH$_2$O |
| 32 | Ph | 5,3-Pye | CH$_2$O |
| 33 | Ph | 6,2-Pye | S |

Assays for Determining Biological Activity

Compounds of Formula I can be tested using the following assays to determine their mammalian leukotriene biosynthesis inhibiting activity.

Human 5-lipoxygenase inhibitor screen

Objective of the Assay: The objective of the assay is to select agents which specifically inhibit the activity of human 5-lipoxygenase using a 100,000×g supernatant fraction prepared from insect cells infected with recombinant baculovirus containing the coding sequence for human 5-lipoxygenase. Enzyme activity is measured spectrophotometrically from the optimal rate of conjugated diene formation ($A_{234}$) measured after the incubation of the enzyme with arachidonic acid in the presence of ATP, calcium ions and phosphatidylcholine.

Description of Procedure: The activity of 5-lipoxygenase is measured using a spectrophotometric assay and recombinant human 5-lipoxygenase as a source of enzyme. The 100,000×g fraction from S19 cells infected with the recombinant baculovirus rvH5LO(8-1) containing the coding region sequence for human 5-lipoxygenase is prepared as described by Denis et al., (J. Biol. Chem., 266, 5072–5079 (1991)). The enzymatic activity is measured, using a spectrophotometric assay from the optimal rate of conjugated diene formation ($A_{234}$) using the procedure described by Riendeau et al., (Biochem. Pharmacol. 38, 2323–2321, (1989)) with minor modifications. The incubation mixture contains 50 mM sodium phosphate pH 7.4, 0.2 mM ATP, 0.2 mM CaCl$_2$, 20 mM arachidonic acid (5 mL from a 100-fold concentrated solution in ethanol), 12 mg/mL phosphatidylcholine, an aliquot of the 100,000×g fraction (2–10 mL) and inhibitor (0.5 mL final volume). Inhibitors are added as 500-fold concentrated solutions in DMSO. Reactions are initiated by the addition of an aliquot of the enzyme preparation and the rate of conjugated diene formation is followed for 2 minutes at room temperature. The reactions are performed in semi-micro cuvettes (0.7 mL capacity, 10 mm path length and 4 mm internal width) and the absorbance changes are recorded with a Hewlett-Packard diode array spectrophotometer (HP 8452A) connected to the ChemStation using UV/VIS Kinetics Software. Enzymatic activity is calculated from the optimal rate of the reaction by a linear fit of the variation of $A_{234}$ during the first twenty seconds using the least square method for the equation $A_{234}=V_o t + A_o$ where $V_o$ is the rate, t is the time, and $A_o$ is the absorbance at zero time. The results are expressed as percentages of inhibition of the reaction rate relative to controls (typically between 0.15–0.21 AU/min.) containing the DMSO vehicle.

Human Polymorphonuclear (PMN) Leukocyte LTB$_4$ Assay

A. Preparation of Human PMN. Human blood is obtained by antecubital venepuncture from consenting volunteers who have not taken medication within the previous 7 days. The blood is immediately added to 10% (v/v) trisodium citrate (0.13M) or 5% (v/v) sodium heparin (1000 IU/mL). PMNs are isolated from anticoagulated blood by dextran sedimentation of erythrocytes followed by centrifugation through Ficoll-Hypaque (specific gravity 1.077), as described by Boyum (*Scand. J. Clin. Lab. Invest.*, 21 (Supp 97), 77 (1968)). Contaminating erythrocytes are removed by lysis following exposure to ammonium chloride (0.16M) in Tris buffer (pH 7.65), and the PMNs are resuspended at $5 \times 10^5$ cells/mL in HEPES (15 mM)-buffered Hanks balanced salt solution containing $Ca^{2+}$(1.4 mM) and $Mg^{2+}$(0.7 mM), pH 7.4.

B. Generation and Radioimmunoassay of $LTB_4$. PMNs (0.5 mL; 2.5×105 cells) are placed in plastic robes and incubated (37° C., 2 min.) with test compounds at the desired concentration or vehicle (DMSO, final concentration 0.2%) as control. The synthesis of $LTB_4$ is initiated by the addition of calcium ionophore A23 187 (final concentration 10 mM) or vehicle in control samples and allowed to proceed for 5 minutes at 37° C. The reactions are then terminated by the addition of cold methanol (0.25 mL) and samples of the entire PMN reaction mixture are removed for radioimmunoassay of $LTB_4$.

Samples (50 mL) of authentic $LTB_4$ of known concentration in radioimmunoassay buffer (R/A) buffer (potassium phosphate 1 mM; disodium EDTA 0.1 mM; Thimerosal 0.025 mM; gelatin 0.1%, pH 7.3) or PMN reaction mixture diluted 1:1 with RIA buffer are added to reaction robes. Thereafter [$^3$H]-$LTB_4$ (10 nCi in 100 mL RIA buffer) and $LTB_4$-antiserum (100 mL of a 1:3000 dilution in RIA buffer) are added and the tubes vortexed. Reactants are allowed to equilibrate by incubation overnight at 4° C. To separate antibody-bound from free $LTB_4$, aliquots (50 mL) of activated charcoal (3% activated charcoal in RIA buffer containing 0.25% Dextran T-70) are added, the robes vortexed, and allowed to stand at room temperature for 10 minutes prior to centrifugation (1500×g; 10 min.; 4° C.). The supernatants containing antibody-bound $LTB_4$ are decanted into vials and Aquasol 2 (4 mL) is added. Radioactivity is quantified by liquid scintillation spectrometry. The specificity of the antiserum and the sensitivity of the procedure have been described by Rokach et al., *Prostaglandins Leukotrienes and Medicine*, 13, 21 (1984). The amount of $LTB_4$ produced in test and control samples is calculated. Inhibitory dose-response curves are constructed using a four-parameter algorithm and from these the $IC_{50}$ values are determined.

Human Whole Blood Assay IN VITRO for $LTB_4$ Production

Fresh blood is collected in heparinized robes by venipuncture from human volunteers. A 500 mL aliquot is incubated with one of the test compounds at final concentrations varying from 3 nM to 3 mM at 37° C. for 15 min. Drug stock solutions are made up in DMSO and 1 mL of the stock solution is added to each assay tube. The blood is then incubated with A23187 (in 5 mL autologous plasma, 25 mM final concentration) at 37° C. for 30 min. At the end of incubation, plasma is obtained (12,000×g, 15 min.) and a 100 mL aliquot is added to 400 mL methanol for protein precipitation. The mixture is vortexed, centrifuged and the supernatant stored at −70° C. until assayed for $LTB_4$ by standard RIA.

Pulmonary Mechanics in Trained Conscious Squirrel Monkeys—A Non-Invasive Technique Objective of the Assay: To assess pulmonary mechanics changes in the airways of conscious squirrel monkeys with the use of a double plethysmograph instead of thoracic catheterization of the pleural space as in the former invasive technique to measure airway resistance (RL) and dynamic compliance ($C_{dyn}$). The non-invasive technique measures changes in the pulmonary parameter "specific airway resistance" (sRaw) which is defined as airway resistance×thoracic gas volume. Agonists like $LTD_4$, 50 mg/mL or *Ascaris suum* antigen (1:25 dilution) aerosol challenge cause an increase in sRaw values, i.e., bronchoconstriction, and consequently allow the evaluation of specific antagonists against these agonists.

For evaluation of compounds in this model, monkeys are fasted overnight and dosed the following morning. The compound is dissolved in 1% methocel solution and given orally at doses ranging from 1 to 0.003 mg/kg in a volume of 1 mL/kg in the home cage. Three hours later the monkeys are placed in a chair within a thoracic plethysmograph whilst the muzzle of the monkey is placed into a nasal plethysmograph through which he breathes. Baseline values for sRaw (cm $H_2O\times sec$.) are taken and at 4 h post compound administration, the monkeys are challenged with an aerosol of the specific agonist. The aerosol is generated by an ultrasonic DeVilbiss nebulizer and administered to the monkeys in the nasal plethysmograph at a rate of 2 liters/minute with the aid of a Pulmo-Aide pump (DeVilbiss, 561 series) for 10 minutes. For data collection, a Buxco Electronics Inc. respiratory computer is utilized which facilitates continuous recording of pulmonary function changes and derives a value for sRaw for each animal.

Following challenge, each minute of data is calculated as a percent change from control values for specific airway resistance (sRaw). The results for each test compound are subsequently obtained for a minimum period of 60 minutes post challenge which are then compared to previously obtained historical baseline control values for that monkey. In addition, the overall values for 60 minutes post-challenge for each monkey (historical baseline values and test values) are averaged separately and are used to calculate the overall percent inhibition of $LTD_4$ or Ascaris antigen response by the test compound. For statistical analysis, paired t-test is used (Reference: Pennock, B. E. et al., *J. Appl. Physiol.: Respirat. Environ. Exercise Physiol.*, 46 (2) 399–406, 1979.

DOG MODEL:

Whole Blood (ex vivo) $LTB_4$ and Urinary $LTE_4$ Excretion Assays

Normal male dogs are anaesthetised, bronchially intubated and catheterised for drug administration and urine collection. After the first urine voiding (15 min.), blood is collected into anticoagulant to define the baseline $LTB_4$ biosynthetic capacity of whole dog blood, and to determine the in vitro potency of this compound in dog blood. Compounds are dissolved in PEG 200/$H_2O$ to a concentration of 0.3 mg/mL. In tubes #1–4, 10 μL of PEG 200 (vehicle) is added to serve as controls. Compounds are titrated from 0.0015 μM–0.37 μM (final concentration). Compounds are added in a volume of 10 μL in ascending concentrations in duplicate (tubes #5–16). The highest drug concentration is also added to robe #17 as a drug blank. To each tube, 500 μL venous blood is added, followed by incubation for 15 minutes at room temperature, without shaking. Tubes #1 & 17, then receives 5 μL of autologous plasma containing 10% DMSO (blanks). 5 μL of autologous plasma containing 10% DMSO and 5 mM A23187 (final 50 μm) are added to robes #2 to 16 to stimulate $LTB_4$ synthesis. Samples are incubated for 30 min. at 37° C., and the reaction terminated by centrifugation. Aliquots of plasma is added to 4 volumes of MeOH, and centrifuged to precipitate proteins prior to analysis of $LTB_4$ content by RIA.

A bolus dose of compounds (0.1, 0.05 or 0.025 mg/kg in PEG200/$H_2O$) is then administered intravenously, followed by a continuous infusion (via a 21 gauge IV catheter) of the compounds (2.5, 0.8 or 0.25 µg/kg/min.). Urine is continuously collected for 1 hour intervals. Sample volumes are recorded, and urinary $LTE_4$ stabilized with 10N NaOH solution (10 µL/mL), prior to freezing (−70° C.). Venous blood is similarly collected (into anticoagulant) contralateral to the IV at hourly intervals. All blood samples are immediately aliquoted (500 µL). To one aliquot, 5 µL of autologous plasma containing 10% DMSO is added as a blank. To other aliquots, 5 µL of autologous plasma containing 10% DMSO and 5 mM A23187 is added (final 50 µM) to stimulate $LTB_4$ synthesis as described above.

Aliquots (10 mL) of thawed urine are centrifuged (10,000×g), and the supernatant adjusted to pH 5.4 with 100 µL glacial acetic acid. As a recovery standard, 3 nCi of [14,15,19,20-$^3$H]-$LTC_4$ (12 pg) is added. Samples are applied to a 3 µm particle $C_{18}$ precolumn, and washed with 2 volumes of 0.1% $NH_4OAc$ buffer pH 5.4. Peptide leukotrienes are then eluted onto a $C_{18}$ analytical HPLC column, and separated with a 66% MeOH/34% 0.1% $NH_4Ac$ pH 5.4 (v/v) mobile phase containing 1 mM EDTA. Fractions eluting with the retention time of synthetic $LTC_4$ (obtained from daily calibration with standards) are collected for estimation of [$^3$H]-$LTC_4$ recovery by scintillation counting. Prior experiments established that recoveries of [$^3$H]-$LTC_4$ and [$^3$H]-$LTE_4$ from dog urine after RP-HPLC are comparable (86.8±1.9% and 83.1±6.1% respectively). In some experiments synthetic $LTE_4$ (0.5 ng/mL) and/or 0.1 nCi [$^3$H]-$LTE_4$ (0.4 pg) are added to certain samples to identify the exact retention time of $LTE_4$. Fractions (0.75 min., 0.75 mL) eluting before, during and after the predicted retention time of synthetic $LTE_4$ (from daily calibration) are collected into sequential wells in a polypropylene microtitre plate, aliquots (200 µL) are removed to identify the retention time of added [$^3$H]-$LTE_4$), and the remainder frozen to −70° C. and lyophilised in a vacuum centrifuge. Fractions are redissolved in 50 µL of 20 mM $Na_2PO_4$ pH 7.2 containing 0.9% NaCl, 0.02% sodium azide, 0.1 mM phenyl methyl sulphonyl fluoride and 1% gelatin and mixed with 2–3 nCi of [14,15,19,20-$^3$H]-$LTE_4$ (5.2–7.8 pg) and an anti-$LTC_4$ mouse monoclonal antibody (21% cross-reactivity with $LTE_4$; final dilution 1/150,000) and incubated for 2 h at 21° C. Free ligand is precipitated by addition of dextran coated charcoal and centrifugation. An aliquot of the supernatant is removed and the concentration of $LTE_4$ immunoactive material estimated by comparison of the unknown bound [$^3$H]-$LTE_4$ against a standard curve derived by serial dilution of a synthetic $LTE_4$ stock solution (4000–7.8 pg/tube). $LTE_4$ concentration is calculated as the immunoreactive material (pg) in n coeluting fractions–n×average background immunoreactive material (pg) in pre- and post-$LTE_4$ fractions, corrected for [$^3$H]-$LTC_4$ recovery, and the fraction volume removed for estimating the retention time of added [$^3$H]-$LTE_4$. Urinary $LTE_4$ excretion (ng/hour) is then calculated from the concentration and excretion volume, and related to values obtained during the first collection on a case by case basis. % inhibition of baseline $LTE_4$ is calculated for the 5–6 and 6–7 h time points, and the mean value obtained for the treatment group. An $ED_{50}$ is then calculated using these values and the infusion dose by non-linear regression analysis (4 parameter fit).

Aliquots (50 µL) of MeOH supernatants of plasma are similarly diluted into 50 µL of the above RIA buffer and mixed with 5–8 nCi of [5,6,8,9,11,12,14,15-$^3$H]-$LTB_4$ (1.7–2.7 pg) and an anti-$LTB_4$ sheep antiserum (final dilution 1/7500). $LTB_4$ is quantified as above against a standard curve derived by serial dilution of a synthetic $LTB_4$ stock solution (1000–1.95 pg/tube). $LTB_4$ generation stimulated by 50 µm A23187 is derived by subtraction of the blank value (DMSO alone) and values are related to those obtained in the first (pre-treatment) sample. An $ED_{50}$ is then calculated using the maximum values for ex vivo inhibition, and the infusion dose, by non-linear regression analysis. For the calculation of in vitro $IC_{50}$ values, blank values for $LTB_4$ production are subtracted from each subsequent value, and the % inhibition calculated for each drug concentration (compared with PEG/$H_2O$). The $IC_{50}$ is then calculated by non-linear regression analysis.

The invention will now be illustrated by the following non-limiting examples in which, unless stated otherwise:

(i) all operations were carried out at room or ambient temperature, that is, at a temperature in the range 18°–25° C.;

(ii) evaporation of solvent was carried out using a rotary evaporator under reduced pressure (600–4000 pascals: 4.5–30 mm. Hg) with a bath temperature of up to 60° C.;

(iii) the course of reactions was followed by thin layer chromatography (TLC) and reaction times are given for illustration only;

(iv) melting points are uncorrected and 'd' indicates decomposition; the melting points given are those obtained for the materials prepared as described; polymorphism may result in isolation of materials with different melting points in some preparations;

(v) the structure and purity of all final products were assured by at least one of the following techniques: TLC, mass spectrometry, nuclear magnetic resonance (NMR) spectrometry or microanalytical data;

(vi) yields are given for illustration only;

(vii) when given, NMR data is in the form of delta (δ) values for major diagnostic protons, given in parts per million (ppm) relative to tetramethylsilane (TMS) as internal standard, determined at 300 MHz or 400 MHz using the indicated solvent; conventional abbreviations used for signal shape are: s. singlet; d. doublet; t. triplet; m. multiplet; br. broad; etc.: in addition "Ar" signifies an aromatic signal;

(viii) chemical symbols have their usual meanings; the following abbreviations have also been used v (volume), w (weight), b.p. (boiling point), m.p. (melting point), L (liter(s)), mL (milliliters), g, (gram(s)), mg (milligrams), mol (moles), mmol (millimoles), eq (equivalent(s)).

PREPARATION OF PHENOLS

Phenol 1

3-Fluoro-5-(4-pyridyl)phenol

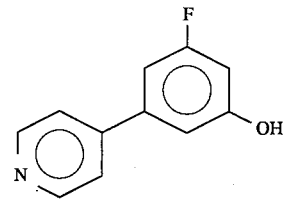

Step 1

4-Tributylstannylpyridine

To a suspension of 4-bromopyridine hydrochloride (1.5 g) in $Et_2O$ (20 mL) at −78° C. was added n-BuLi (6.2 mL of a 2.5M solution). After 30 min. the mixture was warmed to −30° C., tributyltin chloride (2.1 mL) was added and the mixture warmed to 0° C. Saturated NH₄Cl was added and extracted with Et₂O. The organics were washed with H₂O, brine, dried (MgSO₄) and concentrated. Chromatography (silica gel; EtOAc/hexane (15:85)) provided the title compound as an oil.

Step 2

O-Benzyl-3-fluoro-5-(4-pyridyl)phenol

A mixture of 4-tributylstannylpyridine (250 mg), O-benzyl-3-bromo-5-fluorophenol (200 mg; EP 385,662) and tetrakis (triphenylphosphine) palladium (8 mg) in dioxane (3 mL) was heated at 100° C. for 15 h. The solvent was evaporated and the residue chromatographed (silica gel; hexane/EtOAc acetate (4:1–3:2)) to provide the title compound as an oil.

Step 3

3-Fluoro-5-(4-pyridyl)phenol

A mixture of O-benzyl-3-fluoro-5-(4-pyridyl)phenol (120 mg) in thioanisole (1 mL) and CF₃CO₂H (0.6 mL) was heated at 80° C. for 1 h. The mixture was cooled to r.t., made basic with 10N NaOH and extracted with Et₂O. The organics were washed with NaHCO₃, brine, dried (MgSO₄) and concentrated. The residue was triturated with hexane to provide the title compound as a solid.

Phenol 2

3-Fluoro-5-phenylphenol

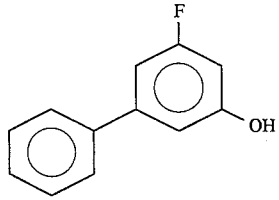

Step 1:

O-(3,4-Dimethoxy)benzyl-3-bromo-5-fluorophenol

To a solution of 3,4-dimethoxybenzyl alcohol (3.5 g) in DMF (40 mL) at 0° C. was added NaH (933 mg; 80% in oil). After stirring for 1 h at r.t., 3,5-difluorobromobenzene (4 g) in DMF (5 mL) was added. After 16 h, the mixture was poured into H₂O (500 mL) and extracted with ethyl acetate. The organics were washed with NH₄OAc buffer, H₂O and brine, dried (MgSO₄) and concentrated. Chromatography of the residue (silica gel; EtOAc/hexane (1:9)) provided the title compound as a white solid.

Step 2:

O-(3.4-Dimethoxy)benzyl-3-fluoro-5-phenylphenol

A mixture of O-(3,4-dimethoxy)benzyl-3-bromo-5-fluorophenol (1 g), benzene boronic acid (500 mg), tetrakis (triphenylphosphine) palladium (200 mg) and 2M Na₂CO₃ (25 mL) in THF (100 mL) was heated at reflux for 3 h. The mixture was extracted with Et₂O and the Et₂O extracts were washed with H₂O and brine. Concentration and chromatography (silica gel; EtOAc/hexane (1:9)) provided the title compound as an oil.

Step 3:

3-Fluoro-5-phenylphenol

A solution of O-(3,4-dimethoxy)benzyl-3-fluoro-5-phenylphenol (930 mg) and DDQ (650 mg) in CH₂Cl₂/H₂O (18:1) was stirred at r.t. for 24 h. The mixture was filtered through celite and the organics were washed with H₂O and concentrated. Chromatography (silica gel; EtOAc/hexane (3:7)) provided the title compound as a solid.

Phenol 3:

3-Fluoro-5-(2-methoxyphenyl)phenol

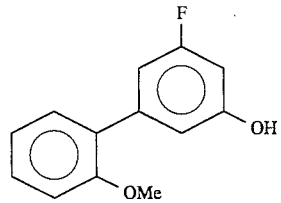

Step 1:

O-(3,4-Dimethoxy)benzyl-3-fluoro-5-(2-methoxyphenyl)phenol

To a solution of 2-bromoanisole (600 mg) in THF (30 mL) at −78° C. was added n-BuLi (1.5 mL of a 2.4M solution). After 10 min., ZnCl₂ (3.2 mL of a 1M solution in THF) was added and the mixture warmed to 0° C. O-(3,4-dimethoxy)benzyl-3-bromo-5-fluorophenol from Phenol 2, Step 1 (1 g) and tetrakis (triphenylphosphine) palladium (200 mg) were added and the mixture was refluxed for 6 h. Saturated NH₄Cl and Et₂O were added. The organic phase was washed with H₂O and brine, dried (MgSO₄) and concentrated. The residue was chromatographed (silica gel; hexane/EtOAc (9:1)) to provide the title compound as an oil.

Step 2:

3-Fluoro-5,(2-methoxyphenyl)phenol

Following the procedure described in Phenol 1, Step 3, but substituting O-(3,4-dimethoxy)benzyl-3-fluoro-5-(2-methoxyphenyl)phenol for O-benzyl-3-fluoro-5-(4-pyridyl)phenol, provided the title compound as a solid.

Phenol 4:

3-Fluoro-5-(3-furyl)phenol

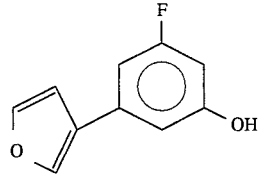

Following the procedures described in Phenol 1, Steps 2 and 3, but substituting 3-tributylstannylfuran for 4-tributylstannylpyridine, and O-(3,4-dimethoxy)benzyl-3-bromo-5-fluorophenol from Phenol 2, Step 1 for O-benzyl-3-bromo-5-fluorophenol, the title compound was obtained as an oil.

Phenol 5:

3-Fluoro-5-(4-fluorophenyl)phenol

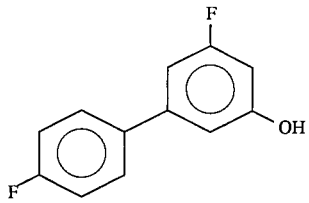

Step 1:

O-(3,4-Dimethoxy)benzyl-3-fluoro-5-(4-fluorophenyl)phenol

To a solution of bromo-4-fluorobenzene (0.2 mL) in THF (5 mL) at −78° C. was added n-BuLi (0.7 mL of a 2.4M solution). After 30 min., trimethyl borate (0.2 mL) was added, the solution warmed to 0° C. and stirred for 45 min. To the mixture was added 2M $Na_2CO_3$ (1.7 mL) and, after 75 min., O-(3,4-dimethoxy)benzyl-3-bromo-5-fluorophenol from Phenol 2, Step 1 (518 mg) and tetrakis (triphenylphosphine) palladium (93 mg). The mixture was refluxed for 6 h, diluted with $Et_2OAc$ and the organics washed with $H_2O$. Drying ($MgSO_4$), concentration and chromatography (silica gel; hexanes/EtOAc (4:1)) provided the title compound.

Step 2:

4-Fluoro-5-(4-fluorophenyl)phenol

Following the procedure described in Phenol 1, Step 3, but substituting O-(3,4-dimethoxy)benzyl-3-fluoro-5-(4-fluorophenyl)phenol for O-benzyl-3-fluoro-5-(4-pyridyl)phenol, provided the title compound as an oil.

Phenol 6:

3-Fluoro-5-(2-pyridyl)phenol

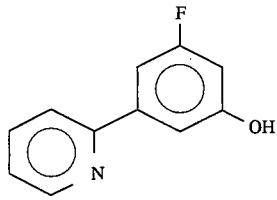

Following the procedures described in Phenol 3, but substituting 2-bromopyridine for 2-bromoanisole, the title compound was obtained as solid.

Phenol 7:

3-Fluoro-5-(3,5-difluorophenyl)phenol

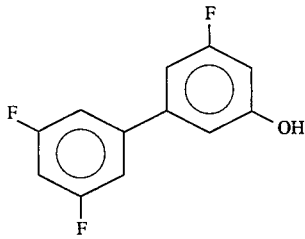

Step 1:

O-(3,4-Dimethoxy)benzyl-3-fluoro-5-(3,5-difluorophenyl)phenol

To magnesium (202 mg) in THF (4 mL) was added bromo-3,5-difluoro-benzene (0.5 mL) and the mixture was refluxed for 30 min. To this mixture were added O-(3,4-dimethoxy)benzyl-3-bromo-5-fluorophenol from Phenol 2, Step 1 (683 mg) and tetrakis (triphenylphosphine) palladium (120 mg) in THF (5 mL) and the mixture was refluxed for 24 h. Concentration and chromatography (silica gel; hexane/EtOAc (4:1)) provided the title compound as an oil.

Step 2:

3-Fluoro-5-(3,5-difluorophenyl)phenol

Following the procedure described in Phenol 1, Step 3, but substituting O-(3,4-dimethoxy)benzyl-3-fluoro-5-(3,5-difluorophenyl)phenol for O-benzyl-3-fluoro-5-(4-pyridyl)phenol, the title compound was obtained as an oil after chromatography (silica gel; hexanes/EtOAc Phenol 8:

3-Fluoro-5-(2-carbomethoxyphenyl)phenol

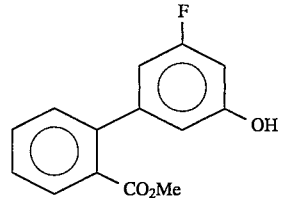

Step 1:

O-(3,4-Dimethoxy)benzyl-3-fluoro-5-trimethylstannylphenol

A mixture of O-(3,4-dimethoxy)benzyl-3-bromo-5-fluorophenol from Phenol 2, Step 1 (1.5 g), hexamethylditin (3 g), lithium chloride (1.5 g) and tetrakis (triphenylphosphine) palladium (200 mg) in dioxane (50 mL) was heated at reflux for 2.5 h. The mixture was cooled to r.t. diluted with $H_2O$ and filtered through celite. The mixture was extracted with $Et_2O$ and the $Et_2O$ extracts were concentrated and the residue chromatographed (silica gel; hexanes/EtOAc (95:5–85:15)) to provide the title compound as an oil.

Step 2:

3-Fluoro-5-(2-carbomethoxyphenyl)phenol

Following the procedures described in Phenol 1, Steps 2 and 3, but substituting O-(3,4-dimethoxy)benzyl-3-fluoro-5-trimethylstannylphenol for 4-tributylstannylpyridine and methyl 2-iodobenzoate for O-benzyl-3-bromo-5-fluorophenol, the title compound was obtained as an oil after chromatography (silica gel; hexane/EtOAc 95:5–85:15)).

Phenol 9:

3-Fluoro-5-(2,4-dichlorophenyl)phenol

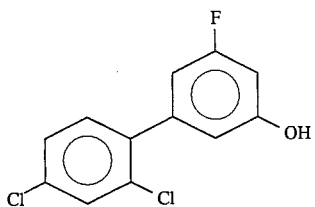

Following the procedures described in Phenol 2, Step 2 and Phenol 1, Step 3, but substituting 2,4-dichlorobenzene boronic acid for benzene boronic acid, provided the title compound as an oil after chromatography (silica gel; hexane/EtOAc (95:5–85:15)).

Phenol 10:

3-Fluoro-5-(2-methylthiophenyl)phenol

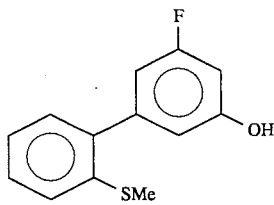

Following the procedures described in Phenol 3, but substituting 2-bromothioanisole for 2-bromoanisole, the title compound was obtained as an oil after chromatography (silica gel; hexane/EtOAc (95:5–90:10)).

Phenol 11:

3-Fluoro-5-(2-methylsulfonylphenyl)phenol

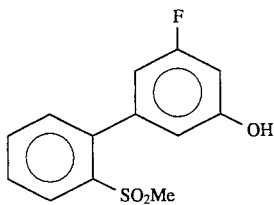

A mixture of 3-fluoro-5-(2-methylthiophenyl)phenol (108 mg) and m-CPBA (230 mg; 80%) in $CHCl_3$ chloroform (4 mL) was stirred for 45 min. Saturated $NaHCO_3$ was added and the mixture was extracted with $Et_2O$. The $Et_2O$ phase was washed with saturated $NaHCO_3$, brine, concentrated and chromatographed (silica gel; hexane/EtOAc (7:3)) to provide the title compound as an oil.

Phenol 12:

3-Fluoro-5-(2-thiazolyl)phenol

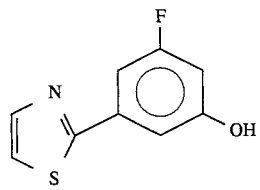

Following the procedures described in Phenol 8, Steps 1 and 2, but substituting O-benzyl-3-bromo-5-fluorophenol for O-(3,4-dimethoxy)benzyl-3-bromo-5-fluorophenol from Phenol 2, Step 1 and 2-bromothiazole for methyl 2-iodobenzoate, the title compound was obtained as an oil after chromatography (silica gel; hexane/EtOAc (97:3–95:5)).

Phenol 13:

3-Fluoro-5-(3-pyridyl)phenol

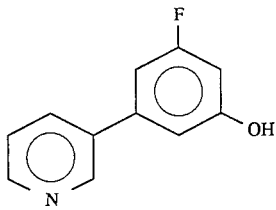

Following the procedures described in Phenol 8, Steps 1 and 2, but substituting O-benzyl-3-bromo-5-fluorophenol for O-(3,4-dimethoxy)benzyl-3-bromo-5-fluorophenol from Phenol 1, Step 1, and 3-bromopyridine for methyl 2-iodobenzoate, the title compound was obtained as an oil after chromatography (silica gel; hexane/ethyl acetate (3:2–1:1)).

Phenol 14:

3-Fluoro-5-(2-thienyl)phenol

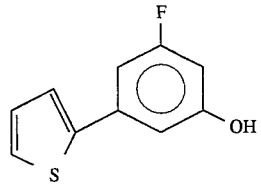

Following the procedures described in Phenol 3, Steps 1 and 2, but substituting thiophene for 2-bromoanisole and O-benzyl-3-bromo-5-fluorophenol for O-(3,4-dimethoxy)benzyl-3-bromo-5-fluorophenol from Phenol 1, Step 1, the title compound was obtained as an oil after chromatography (silica gel; hexane/EtOAc (90:10–85:15)).

PREPARATION OF THIOPHENOLS

Thiophenol 1:

3-Fluoro-5-phenylthiophenol

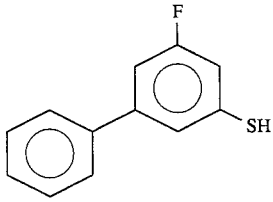

Step 1:

1,3-Difluoro-5-phenylbenzene

Following the procedures described in Phenol 2, Step 2, but substituting 3,5-difluorobromobenzene for O-(3,4-dimethoxy)benzyl-3-bromo-5-fluorophenol, the title compound was obtained as a liquid.

Step 2:

S-(2-Trimethylsilylethyl)-3-fluoro-5-phenylthiophenol

To a suspension of NaH (360 mg) in DMF (10 mL) at 0° C. was added 2-(trimethylsilyl)ethanethiol (1.8 mL). After 10 min., a solution of 1,3-difluoro-5-phenylbenzene (1.9 g) in DMF (5 mL) was added and the resulting mixture was heated at 110° C. for 2.5 h. Ethyl acetate was added and the solution was washed with 1N HCl, H₂O and brine. Concentration and chromatography (silica gel; hexane/EtOAc (98:2)) provided the title compound as a liquid.

Step 3:

3-Fluoro-5-phenylthiophenol

To S-(2-trimethylsilylethyl)-3-fluoro-5-phenylthiophenol (2.4 g) in DMF (50 mL) was added Bu₄NF (16 mL of a 1M THF solution). After 90 min., EtOAc was added and this solution was washed with 1N HCl, H₂O and brine. Concentration and chromatography (silica gel; hexane/EtOAc (9:1)) provided the title compound as a liquid.

Thiophenol 2:

3-Fluoro-5-(4-fluorophenyl)thiophenol

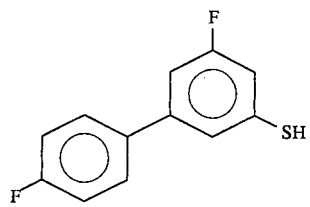

Step 1:

S-(2-Trimethylsilylethyl)-3-bromo-5-fluorothiophenol

Following the procedure described in Thiophenol 1, Step 2 but substituting 3,5-difluorobromobenzene for 1,3-difluoro-5-phenylbenzene and stirring at 0° C. rather than 110° C., the title compound was obtained as a liquid.

Step 2:

S-(2-Trimethylsilylethyl)-3-fluoro-5-(4-fluorophenyl) thiophenol

Following the procedure described in Phenol 3, Step 1, but substituting S-(2-trimethylsilylethyl)-3-bromo-5-fluorothiophenol for 2-bromoanisole and 4-fluoroiodobenzene for O-(3,4-dimethoxy)benzyl-3-bromo-5-fluorophenol from Phenol 2, Step 1, the title compound was obtained as a liquid.

Step 3:

3-Fluoro-5-(4-fluorophenyl)thiophenol

Following the procedure described in Thiophenol 1, Step 3, but substituting S-(2-trimethylsilylethyl)-3-fluoro-5-(4-fluorophenyl)thiophenol for S-(2-trimethylsilylethyl)-3-fluoro-5-phenylthiophenol, the title compound was obtained as a liquid.

Thiophenol 3:

3-Fluoro-5-(3-pyridyl)thiophenol

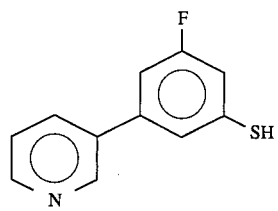

Step 1:

1,3-Difluoro-5-(3-pyridyl)benzene

Following the procedure described in Phenol 3, Step 1, but substituting 3-bromopyridine for 2-bromoanisole and 3,5-difluorobromobenzene for O-(3,4-dimethoxy)benzyl-3-bromo-5-fluorophenol from Phenol 2, Step 1, the title compound was obtained as a solid.

Step 2:

3-Fluoro-5-(3-pyridyl)thiophenol

Following the procedure described in Thiophenol 1, Steps 2 and 3, but substituting 1,3-difluoro-5-(3-pyridyl)benzene for 1,3-difluoro-5-phenylbenzene, the title compound was obtained as a solid.

PREPARATION OF PYRIDINES

Pyridine 1:

2-Hydroxymethyl-6-phenylpyridine

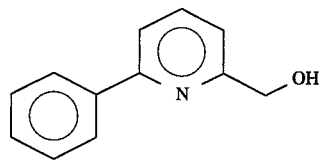

Step 1:

2-(tert-Butyldiphenylsiloxy)methyl-6-phenylpyridine

A mixture of 2-bromo-6-(tert-butyldiphenylsiloxy)methylpyridine (1 g; WO 94/00444), benzeneboric acid (400 mg) and tetrakis (triphenylphosphine) palladium (200 mg) in 2M Na₂CO₃ (25 mL) and THF (100 mL) was refluxed for 16 h. The THF was evaporated and the residue was extracted with EtOAc. The organics were dried (MgSO₄), concentrated and chromatographed (silica gel; hexane/ethyl acetate (20:1)) to provide the title compound as a solid.

Step 2:

2-Hydroxymethyl-6-phenylpyridine

To a solution of 2-(tert-butyldiphenylsiloxy)methyl-6-phenylpyridine (1.2 g) in THF (20 mL) was added Bu₄NF (3.3 mL of a 1M solution in THF). After 1 h, NH₄OAc buffer was added and the mixture extracted with EtOAc. The organics were dried (MgSO₄), concentrated and chromatographed (silica gel; hexane/EtOAc acetate (3:2)) to provide the title compound as a solid.

Pyridine 2:

2-Hydroxymethyl-6-(4-chlorophenyl)pyridine

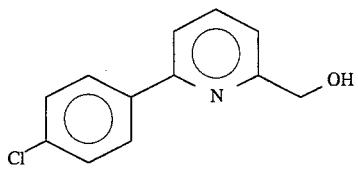

Following the procedures described in Pyridine 1, Steps 1 and 2 but substituting 4-chlorobenzene acid for benzeneboric acid, the title compound was obtained as a solid.

Pyridine 3:

2-Hydroxymethyl-6-(4-fluorophenyl)pyridine

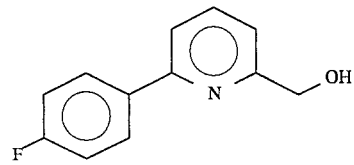

Step 1:

2-(tert-Butyldiphenylsiloxy)methyl-6-(4-fluorophenyl)pyridine

A mixture of 2-bromo-6-(tert-butyldiphenylsiloxy)methylpyridine (1 g; WO 94/00444), 4-fluorophenylmagnesium bromide (3.5 mL of a 2M solution in $Et_2O$) and tetrakis (triphenylphosphine) palladium (200 mg) in THF (20 mL) was refluxed for 4 h. To the mixture was added $NH_4OAc$ buffer and the mixture was extracted with EtOAc. The organics were dried ($MgSO_4$), concentrated and chromatographed (silica gel; hexane/EtOAc (30:1)) to provide the title compound as an oil.

Step 2:

2-Hydroxymethyl-6-(4-fluorophenyl)pyridine

Following the procedure described in Pyridine 1, Step 2, but substituting 2-(tert-butyldiphenylsiloxy)methyl-6-(4-fluorophenyl)pyridine for 2-(tert-butyldiphenylsiloxy)methyl-6-phenylpyridine, the title compound was obtained as a solid.

Pyridine 4:

3-Hydroxymethyl-5-phenylpyridine

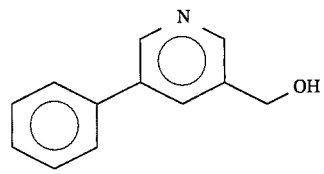

Step 1:

Methyl 5-Phenylnicotinate

A mixture of methyl 5-bromonicotinate (750 mg), benzeneboric acid (600 rag) and tetrakis (triphenylphosphine) palladium (200 mg) in 2M $Na_2CO_3$ (25 mL) and THF (100 mL) was refluxed for 16 h. The THF was evaporated and the residue was extracted with EtOAc. The organics were dried ($MgSO_4$), concentrated and chromatographed (silica gel; hexane/EtOAc (3:1)) to provide the title compound as a solid.

Step 2:

3-Hydroxymethyl-5-phenylpyridine

To a solution of methyl 5-phenylnicotinate (640 mg) in THF (20 mL) at 0° C. was added $LiAlH_4$ (3 mL of a 1M solution). After 1 h, $H_2O$ (0.12 mL), 15% sodium hydroxide (0.12 mL) and $H_2O$ (0.36 mL) were added successively. The mixture was filtered, washing with EtOAc. The filtrate was concentrated and chromatographed (silica gel; EtOAc/hexane (4:1–5:1)) to provide the title compound as a solid.

Pyridine 5:

2-Bromo-6-phenylpyridine

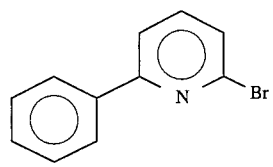

To a solution of 2,6-dibromopyridine (2 g) in THF (100 mL) at −100° C. was added n-BuLi (6 mL of a 1.4M solution in hexane) over 10 min. After stirring for 20 min., $ZnCl_2$ (17 mL of a 0.5M solution in THF) was added. The cold bath was removed and after 40 min., iodobenzene (0.94 mL) and tetrakis (triphenylphosphine) palladium (390 mg) were added and the mixture stirred at r.t. for 20 h. Ethyl acetate was added and the organics were washed with $NaHCO_3$, $H_2O$ and brine, dried ($MgSO_4$) and concentrated. Chromatography (silica gel; hexane/EtOAc (97:3)) provided the title compound as a solid.

PREPARATION OF QUINOLINES

Quinoline 1:

7-Bromomethyl-2-cyano-4-(3-furyl)quinoline

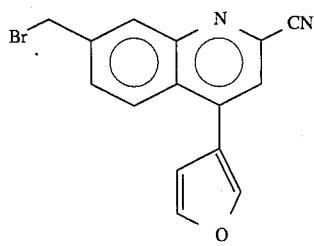

Step 1:

7-Chloro-4-iodoquinoline 4,7-Dichloroquinoline (50 g) was added, in small portions, to HI (425 mL) at r.t. and then heated at 130° C. for 5 h. The mixture was cooled, poured into ice/$H_2O$ (600 mL), made basic (pH 10) with 10N NaOH, and extracted with $CHCl_3$. The combined organics were washed with $NH_4OAc$ buffer, 10% $Na_2S_2O_3$ and brine. Drying ($Na_2SO_4$) and concentration provided the title compound that was used as such.

Step 2:

7-Chloro-4-(3-furyl)quinoline

To a solution of 3-bromofuran (30 g) in Et$_2$O (400 mL) at −78° C. was added n-BuLi (89.3 mL of a 2.4M solution in hexane). After stirring for 40 min., B(OMe)$_3$ (25.5 mL) was added and the mixture was stirred at −78° C. for 30 min., followed by 30 min. at 0° C. Na$_2$CO$_3$ (196 mL of a 2M solution) was then added and the mixture stirred at 0° C. for 3 h. The Et$_2$O was evaporated and replaced by THF (730 mL). 7-Chloro-4-iodoquinoline (53.7 g) and palladium tetrakis (triphenylphosphine) (10.7 g) were added and the mixture was heated at reflux for 12 h. The mixture was cooled to r.t. the layers were separated and the THF phase was concentrated. The aqueous phase was extracted with EtOAc and combined with the residue from the THF phase. The organics were washed with H$_2$O, brine, dried (MgSO$_4$) and concentrated. Chromatography (silica gel; EtOAc/hexane (1:9)) provided the title compound as a beige solid.

Step 3:

4-(3-Furyl)-7-methylquinoline

To a mixture of 7-chloro-4-(3-furyl)quinoline (30.2 g) and NiCl$_2$(dppp) (7.1 g) in Et$_2$O (950 mL) was added MeMgBr (141 mL of a 1.4M solution in 3:1 THF:toluene) at such a rate to maintain a temperature of 30° C. The mixture was refluxed for 30 min., cooled to 0° C. and saturated NH$_4$Cl (200 mL) was added followed by H$_2$O (100 mL). The layers were separated and the aqueous phase was extracted with EtOAc. The combined organics were washed with NH$_4$OAc buffer, brine, dried (MgSO$_4$) and concentrated. Chromatography (silica gel; EtOAc/hexane (3:7)) provided the title compound as a beige oil.

Step 4:

2-Cyano-4-(3-furyl)-7-methylquinoline

To a solution of 4-(3-furyl)-7-methylquinoline (24.9 g) in CHCl$_3$ (900 mL) was added m-CPBA (30.8 g; 80%) portionwise. After 1 h, saturated sodium NaHCO$_3$ was added followed by H$_2$O (150 mL). The aqueous phase was extracted with CHCl$_3$ and the combined organics were washed with saturated NaHCO$_3$, brine, dried (Na$_2$SO$_4$) and concentrated. The residue was dissolved in CH$_2$Cl$_2$ (900 mL) and TMSCN (19 mL) was added. After 5 min., dimethylcarbamyl chloride (13.1 mL) was added and the mixture was stirred for 12 h at r.t. Potassium carbonate (10%; 400 mL) was slowly added and the aqueous layer was extracted with CH$_2$Cl$_2$. The combined organics were washed with 10% K$_2$CO$_3$, NH$_4$OAc buffer, brine, dried (Na$_2$SO$_4$) and concentrated. Chromatography (silica gel; EtOAc/hexane (1:9–2:3)) provided the title compound as a solid.

Step 5:

7-Bromomethyl-2-cyano-4-(3-furyl)quinoline

To a solution of 2-cyano-4-(3-furyl)-7-methylquinoline (4.2 g) in refluxing CCl$_4$ (400 mL) was added NBS (3.3 g) and AIBN (150 mg) portionwise. After 90 min., the mixture was cooled to r.t. and filtered through a pad of silica gel washing with CH$_2$Cl$_2$. The filtrate was concentrated and swished with Et$_2$O for 15 h. The solid precipitate was collected and NMR analysis indicated that it contained 85% of the title compound. This material was used as such in the subsequent reactions.

PREPARATION OF COUMARINS

Coumarin 1:

4-(3-Furyl)-7-bromomethylcoumarin

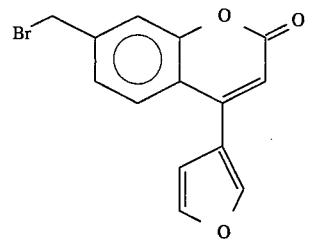

Step 1:

3-Acetoxytoluene

To a solution of m-cresol (Aldrich) (80 g, 0.74 mol) in dry CH$_2$Cl$_2$ (300 mL) and pyridine (71 mL, 0.89 mol) at 0° C. was added dropwise AcCl (58 mL, 0.81 mol). The reaction mixture was stirred for ca 1 h and then diluted with more CH$_2$Cl$_2$. The organic phase was washed successively with HCl 1N (3×), brine, dried over MgSO$_4$ and evaporated. The residue was distilled under vacuum to give the title compound.

Step 2:

4-Methyl-2-hydroxyacetophenone

To 50 g (0.33 mol) of 3-acetoxytoluene from Step 1 was added AlCl$_3$ (60 g, 0.45 mol) and the resulting mixture was heated at 165° C. for 20 min., then cooled to 0° C. and HCl 1N was carefully added followed by Et$_2$O. The aqueous phase was extracted 5× with Et$_2$O and the combined organic phase was washed with brine, dried over MgSO$_4$ and evaporated. The residue was distilled under vacuum to give the title compound.

Step 3:

4-Hydroxy-7-methylcoumarin

A solution of 42 g (0.28 mol) of 4-methyl-2-hydroxyacetophenone in benzene (150 mL) was added over 30 min., to a suspension of NaH (50% oil), (30 g, 0.63 mol) in 400 mL of benzene at reflux. Then diethylcarbonate (67.8 mL, 0.56 mol) in benzene (500 mL) was added over 15 min. The reaction mixture was refluxed for 16 h and more NaH (13 g, 0.28 mol) was added followed by more diethylcarbonate (33 g, 0.28 mol). After another 6 h at reflux the reaction mixture was cooled to room temperature and 2N HCl was added (1.5 L) to form a white precipitate. The solid was then filtered and added to a solution of NaOH (4N, 800 mL). The resulting basic solution was then extracted with Et$_2$O (2×500 mL) and the basic solution acidified with conc. HCl to give a white solid which, after filtration and drying, gave the title compound.

Step 4:

4-Trifluoromethanesulfonyloxy-7-methylcoumarin

To a solution of 4-hydroxy-7-methylcoumarin (10 g, 56.8 mmol) in CH$_2$Cl$_2$ (250 mL) and Et$_3$N (9.5 mL, 68.2 mmol) at 0° C. was added trifluoromethanesulfonic anhydride (11.5 mL, 68.2 mmol). The reaction mixture was stirred for 16 h. Then more CH$_2$Cl$_2$ was added and washed with 1N HCl (3×), brine dried over MgSO$_4$ and evaporated. The residue was purified by flash chromatography on silica gel using hexane/EtOAc (9:1) to give the title compound.

Step 5:

4-(3-Furyl)-7-methylcoumarin

To a solution of 3-bromofuran (1.9 g, 12.7 mmol) in dry Et$_2$O (30 mL) at −70° C. was added BuLi in hexane (1.9M, 6.7 mL, 12.7 mmol) and the resulting mixture was stirred for 20 min. Trimethylborate (Aldrich) (1.4 mL, 12.7 mmol) was added dropwise and the mixture stirred for 20 min. A solution of the triflate from Step 4 in THF: H$_2$O (24 mL, 6 mL) containing (Ph$_3$P)$_4$Pd (1.1 g, 0.97 mmol) was added and the reaction was heated to reflux for 16 h. The reaction mixture was cooled to r.t. and EtOAc was added and the organic phase washed with H$_2$O (3×), brine, dried over MgSO$_4$ and evaporated to give a white solid. A swish in EtOAc gave, after filtration, 1.8 g (82%) of the title compound.

Step 6:

7-Bromomethyl-4-(3-furyl)coumarin

To a solution of 7-bromomethyl-4-(3-furyl)coumarin (1.2 g, 5.3 mmol) in CCl$_4$ (40 mL) was added NBS (1 g, 5.8 mmol) followed by bis azoisobutyronitrile (87 mg, 0.53 mmol). The resulting mixture was refluxed for 4 h, then cooled to r.t. filtered and evaporated. Purification by chromatrography on silica gel gave the title compound.

Coumarin 2:

4-(3-Furyl)-7-bromocoumarin

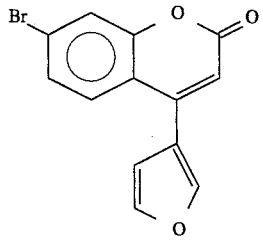

Following the procedures described for Coumarin 1, Steps 1 to 5, but substituting 3-bromophenol for m-cresol, the title compound was obtained.

Coumarin 3:

4-Phenyl-7-bromomethylcoumarin

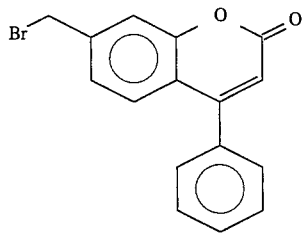

Following the procedures described for Coumarin 1, but substituting iodobenzene for 3-bromofuran, the title compound was obtained.

Coumarin 4:

4-(3-Furyl)-7-mercaptocoumarin

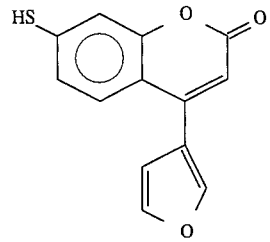

Step 1:

7-(2-Trimethylsilylethylthio)-4-(3-furyl)coumarin

A mixture of 7-bromo-4-(3-furyl)coumarin (Coumarin 2) (1.5 g, 5.15 mmol), 2-(trimethylsilyl)ethanethiol (830 mg, 6.18 mmol), and K$_2$CO$_3$ (1.77 g, 12.9 mmol) in NMP (12 mL) was heated at 105° C. for 4 h. After cooling, there was added saturated aqueous NH$_4$Cl (10 mL), then H$_2$O (50 mL) and the mixture was extracted twice with EtOAc. The organic extracts were washed 4 times with H$_2$O, dried over MgSO$_4$ and evaporated down to a residue which was chromatographed on silica gel eluting with a 1:3 mixture of EtOAc and hexane, to afford the title compound as a tan solid.

Step 2:

4-(3-Furyl)-7-mercaptocoumarin

The coumarin from Step 1 (963 mg) was dissolved in DMF (25 mL) and to this solution there was added Bu$_4$NF 1M in THF (8.4 mL). The mixture was stirred at r.t. for 2 h, poured onto 1N aqueous HCl (50 mL), diluted with H$_2$O (50 mL) and filtered to afford the title compound as a tan solid.

Coumarin 5:

4-(3-Pyridyl)-7-bromocoumarin

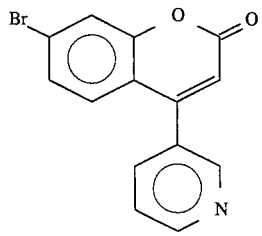

Step 1:

7-Bromo-4-trifluoromethonesulfonyloxycoumarin

Following the procedures described for Coumarin 1, Steps 1 to 4, but substituting 3-bromophenol for m-cresol, the title compound was obtained.

Step 2:

4-(3-Pyridyl)-7-bromocoumarin

To a solution of 3-bromopyridine (0.10 mL) in THF (3 mL) stirred at −100° C. was added a solution of n-BuLi in hexane (1.4M; 0.71 mL), after 10 min., the resulting yellow-green solution was treated with a solution of ZnCl$_2$ in THF (0.5M; 2 mL) and the cold bath was removed. After another 10 min., triflate from Step 1 (376 mg) and tetrakis (triphenylphosphine)palladium(0) were added and the reaction mixture was stirred at r.t. for 1 h. Ethyl acetate was then added and the organic phase was washed successively with saturated aqueous NaHCO$_3$, H$_2$O and brine dried (MgSO$_4$), and evaporated. Flash chromatography of the residue (silica gel; hexane/EtOAc (1:3)) afforded the title compound as a yellow solid.

Coumarin 6:

4-(4-Fluorophenyl)-7-bromocoumarin

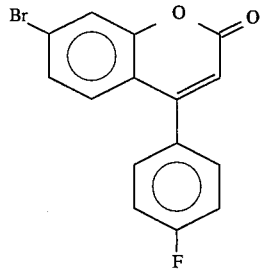

Following the procedures described for Coumarin 1, Steps 1 to 5, but substituting 3-bromophenol for m-cresol and 4-fluoroiodobenzene for 3-bromofuran, the title compound was obtained.

Coumarin 7:

4-(3-Pyrrolyl)-7-bromocoumarin

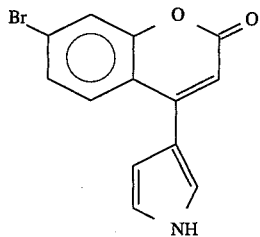

Step 1:

7-Bromo-4-(1-triisopropylsilyl-1-H-pyrrol-3-yl)coumarin

The triflate from Coumarin 5, Step 1 (298 mg, 0.8 mmole) was mixed with 1-(triisopropylsilyl)-3-(tributylstannyl)pyrrole (451 mg, 0.88 mmole) (prepared as described by Alvarez A. et al., *J. Org. Chem.*, 57, 1653, 1992) tetrakis (triphenylphosphine) palladium (37 mg, 0.032 mmole) and LiCl (101.7 mg, 2.4 mmol) in dioxane (2.0 mL) and the mixture was heated at reflux for 2.5 h. The reaction mixture was diluted in EtOAc, washed with brine, dried over MgSO$_4$, filtered and evaporated to give an oil which was purified on a silica column using toluene as the eluent. The title compound was obtained as an oil.

Step 2:

4-(3-Pyrrolyl)-7-bromocoumarin

To a solution of the silyl compound from Step 1 (42 mg, 0.094 mmol) in THF (1 mL) was added Bu$_4$NF 1M in THF (94 (L, 0.094 mmol) and the reaction mixture was stirred at r.t. for 15 min. The mixture was diluted with EtOAc, washed with brine, dried over MgSO$_4$, filtered and evaporated to give the title compound as an oil.

Coumarin 8:

4-(4-Oxazolyl)-7-bromocoumarin

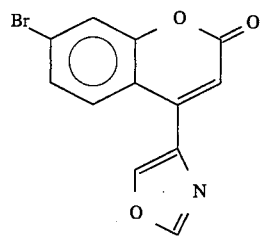

Step 1:

7-Bromo-4-(1-ethoxyvinyl)coumarin

A mixture of triflate (from Coumarin 5, Step 1) (2.88 g), (1-ethoxyvinyl)tributyltin (3.06 g), tetrakis (triphenylphosphine)palladium (0) (0.36 g) and LiCl (0.98 g) in dioxane (20 mL) was refluxed for 4 h. Ethyl acetate was then added and the organic phase was washed with H$_2$O and brine, dried (MgSO$_4$) and evaporated. Flash chromatography of the residue (silica gel; hexane/EtOAc (9:1)) afforded the title compound as a yellow solid.

Step 2:

7-Bromo-4-(2-bromoacetyl)coumarin

To a solution of vinyl ether from Step 1 (1.02 g) in CH$_3$CN:H$_2$O 4:1 (25 mL) were successively added NBS (0.82 g) and concentrated HBr (20 µL). After being stirred at r.t. for 4 h. The reaction mixture was treated with 5% aqueous NaHSO$_3$ (1 mL). Ethyl acetate was then added and the organic phase was washed with saturated aqueous NaHCO$_3$, H$_2$O and brine, dried (MgSO$_4$) and evaporated. Flash chromatography of the residue (silica gel; hexane/EtOAc (85:15)) afforded the title compound as a white solid.

Step 3:

4-(4-Oxazolyl)-7-bromocoumarin

A solution of α-bromoketone from Step 2 (122 mg) and sodium formate (47 mg) in DMF (1.2 mL) was stirred at r.t. for 4 h before EtOAc was added. The organic phase was washed with H$_2$O (2×) and brine, dried (MgSO$_4$) and evaporated in afford the corresponding formate in a crude form that was used in the next step without further purification. The formate was refluxed in AcOH (1 mL) with NH$_4$OAc (135 mg) for 90 min. EtOAc was then added and the organic phase was washed with H$_2$O, saturated aqueous NaHCO$_3$ and brine, dried (MgSO$_4$) and evaporated. Flash chromatography of the residue (silica gel; hexane/EtOAc (85:15)) afforded the title compound as a yellow solid.

PREPARATION OF NAPHTHALENES

Naphthalene 1:

2-Cyano-4-(3-furyl)-7-mercaptonaphthalene

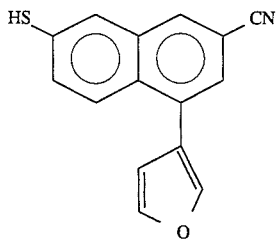

Step 1:

2-Cyano-4-(3-furyl)-7-iodonaphthalene

To a suspension of 7-cyano-5-(3-furyl)-2-naphthol (9.4 g; WO 94/00444) in $CH_2Cl_2$ (100 mL) and pyridine (4.9 mL) at 0° C. was added triflic anhydride (10 mL) and the mixture was stirred at r.t. for 2.5 h. $CH_2Cl_2$ was added and the mixture was washed with $H_2O$, dried ($MgSO_4$) and concentrated. Chromatography (silica gel; hexane/EtOAc (5:1)) provided the triflate derivative as an oil. A portion of this material (9.5 g), hexamethylditin (17 g), LiCl (4.4 g) and tetrakis (triphenylphosphine)palladium (1.2 g) in dioxane (100 mL) was refluxed for 1 h. The mixture was cooled to r.t., diluted with $Et_2O$ and the solids were removed by recantation. Iodine (21 g) in $Et_2O$ (200 mL) was added to this solution and, after 1 h, the mixture was washed successively with $H_2O$, 10% $Na_2S_2O_3$, $H_2O$ and dried ($MgSO_4$). Concentration and chromatography (silica gel; hexane/EtOAc (9:1)) provided the title compound as a solid.

Step 2:

2-Cyano-4-(3-furyl)-7-mercaptonaphthalene

A mixture of 2-cyano-4-(3-furyl)-7-iodonaphthalene (1 g), 2-(trimethylsilyl)ethane thiol (390 mg), potassium tert-butoxide (650 mg) and tetrakis (triphenylphosphine)palladium (100 mg) in EtOH (5 mL) was reluxed for 90 min. The solvent was evaporated and the residue partitioned between $Et_2O$ and $H_2O$. The organic phase was dried ($MgSO_4$) and concentrated and the residue was dissolved in DMF (24 mL). To this solution was added $Bu_4NF$ (7.7 mL of a 1M THF solution). After 30 min., 1N HCl was added followed by $H_2O$. The precipitate that formed was filtered and washed with $H_2O$ to provide the title compound as a solid.

PREPARATION OF ISOQUINOLINES

Isoquinoline 1:

7-Iodo-4-phenylisoquinoline

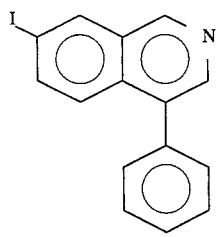

Step 1:

7-Methoxy-4-phenylisoquinoline

To a solution of 3-methoxybenzylamine (15 g) and pyridine (15 mL) in $CH_2Cl_2$ (100 mL) at 0° C. was added p-toluenesulfonyl chloride (21 g) portionwise. After addition was complete, the mixture was stirred at r.t. for 2 h and then saturated $NH_4Cl$ was added. The mixture was extracted with $Et_2O$ and the extracts were washed with $H_2O$, brine, dried ($MgSO_4$) and concentrated. The residue, 2-bromoacetophenone (23 g) and $Cs_2CO_3$ (45 g) in acetone (400 mL) was stirred at r.t. for 20 h. The acetone was evaporated and saturated $NH_4Cl$ was added. The mixture was extracted with EtOAc and the organics were washed with $H_2O$, brine, dried ($MgSO_4$) and concentrated. The residual solid was swished in $Et_2O$ for 3 h and then mixed with $CF_3CO_2H$ (17 mL). After heating at 75° C. for 2.5 h, the mixture was cooled to r.t., EtOAc and $H_2O$ were added and the aqueous phase was made basic by the careful addition of solid $K_2CO_3$. The organic phase was washed with saturated $NaHCO_3$, $H_2O$, brine and dried ($MgSO_4$). Concentration and chromatography (silica gel; hexane/EtOAc (3:2–1:1)) provided the title compound as a solid.

Step 2:

7-Trifluoromethanesulfonyloxy-4-phenylisoquinoline

A mixture of 7-methoxy4-phenylisoquinoline (8.8 g) and pyridine hydrochloride (30 g) was heated at 195°–200° C. for 4.5 h. The mixture was cooled and $H_2O$ was added. After stirring for 30 min., the precipitate that formed was isolated by filtration, washing with $H_2O$. The residual solid was swished with EtOAc for 90 min. To a portion of this material (3 g) and pyridine (5.5 mL) in $CH_2Cl_2$ (100 mL) at 0° C. was added triflic anhydride (2.8 mL) and the mixture was stirred at 0° C. for 30 min. and then at r.t. for 90 min. Saturated $NH_4Cl$ was added and the mixture extracted with $CH_2Cl_2$. The organics were washed with $H_2O$, brine, dried ($MgSO_4$) and concentrated. Chromatography (silica gel; hexane/EtOAc (4:1)) provided the title compound as a solid.

Step 3:

7-Iodo-4-phenylisoquinoline

A mixture of 7-trifluoromethanesulfonyloxy-4-phenylisoquinnoline (2.7 g), hexamethylditin (7.4 g), LiCl (1.9 g) and tetrakis(triphenylphosphine)palladium (500 mg) in dioxane (50 mL) was heated at 90° C. for 1 h. The mixture was cooled, filtered through celite and the filtrate was concentrated. The residual material was dissolved in $CHCl_3$ (59 mL) and solid $I_2$ (1.8 g) was added and the resulting mixture was stirred at r.t. for 1 h. The reaction mixture was quenched with $Na_2S_2O_3$ solution and the organic layer was decanted, washed with $H_2O$, brine, dried ($MgSO_4$) and concentrated. Chromatography (silica gel; hexane/EtOAc (10:1–7:3) provided the title compound as an oil.

EXAMPLE 1

2-Cyano-4-(3-furyl)-7-[5-(4-pyridyl)-3-fluorophenoxymethyl]quinoline

A mixture of Phenol 1 (28 mg), Quinoline 1 (60 mg) and $Cs_2CO_3$ (70 mg) in DMF (3 mL) was stirred for 15 h at r.t. $H_2O$ was added and the mixture was extracted with $Et_2O$. The organics were washed with $H_2O$, brine, dried ($MgSO_4$) and concentrated. Trituration with $Et_2O$ provided the title compound as a white solid, m.p.>200° C. (dec.).

$^1$H NMR (300 MHz, (CD$_3$)$_2$CO): δ5.59 (s, 2H), 7.04 (d, 1H), 7.06 (s, 1H), 7.18 (d, 1H), 7.40 (s, 1H), 7.70 (app.d, 2H), 7.90 (s, 1H), 7.95 (m, 2H), 8.20 (s, 1H), 8.30 (s, 1H), 8.40 (d, 1H), 8.60 (m, 2H).

EXAMPLE 2

2-Cyano-4-(3-furyl)-7-(5-phenyl-3-fluorophenoxymethyl)quinoline

Following the procedures described in Example 1, but substituting Phenol 2 for Phenol 1, the title compound was obtained as a pale yellow solid, m.p. 150.5°–152° C.

EXAMPLE 3

2-Cyano-4-(3-furyl)-7-[5-(2-methoxyphenyl)-3-fluorophenoxymethyl]quinoline

Following the procedures described in Example 1, but substituting Phenol 3 for Phenol 1, the title compound was obtained as a white solid, m.p. 132.5°–134.5° C.

EXAMPLE 4

2-Cyano-4-(3-furyl)-7-[5-(3-furyl)-3-fluorophenoxymethyl]quinoline

Following the procedures described in Example 1, but substituting Phenol 4 for Phenol 1, the title compound was obtained as a white solid, m.p. 156°–159° C.

EXAMPLE 5

2-Cyano-4-(3-furyl)-7-(4-phenylphenoxymethyl)quinoline

Following the procedures described in Example 1, but substituting 4-phenylphenol for Phenol 1, the title compound was obtained as a white solid, 181°–183 ° C.

EXAMPLE 6

2-Cyano-4-(3-furyl)-7-[5-(4-fluorophenyl)-3-fluorophenoxymethyl]quinoline

Following the procedures described in Example 1, but substituting Phenol 5 for Phenol 1, the title compound was obtained as a solid, m.p. 177°–180° C.

EXAMPLE 7

2-Cyano-4-(3-furyl)-7-[5-(2-pyridyl)-3-fluorophenoxymethyl]quinoline

Following the procedures described in Example 1, but substituting Phenol 6 for Phenol 1, the title compound was obtained as a solid, m.p. 198°–200° C.

EXAMPLE 8

2-Cyano-4-(3-furyl)-7-[5-(3,5-difluorophenyl)-3-fluorophenoxymethyl]quinoline

Following the procedures described in Example 1, but substituting Phenol 7 for Phenol 1, the title compound was obtained as a solid, m.p. 189°–192° C.

EXAMPLE 9

2-Cyano-4-(3-furyl)-7-[5-(2-carbomethoxyphenyl)-3-fluorophenoxymethyl]-quinoline Following the procedures described in Example 1, but substituting Phenol 8 for Phenol 1, the title compound was obtained as a solid, m.p. 152.5°–153.5° C.

EXAMPLE 10

2-Cyano-4-(3-furyl)-7-[5-(2,4-dichlorophenyl)-3-fluorophenoxymethyl]quinoline

Following the procedures described in Example 1, but substituting Phenol 9 for Phenol 1, the title compound was obtained as a solid, m.p. 188°–190° C.

EXAMPLE 11

2-Cyano-4-(3-furyl)-7-[5-(2-methylthiophenyl)-3-fluorophenoxymethyl]quinoline

Following the procedures described in Example 1, but substituting Phenol 10 for Phenol 1, the title compound was obtained as a solid, m.p. 166.5°–168.5° C.

EXAMPLE 12

2-Cyano-4-(3-furyl)-7-[5-(2-methylsulfonylphenyl)-3-fluorophenoxymethyl]quinoline Following the procedures described in Example 1, but substituting Phenol 11 for Phenol 1, the title compound was obtained as a solid, m.p. 186°–187° C.

EXAMPLE 13

2-Cyano-4-(3-furyl)-7-[5-(2-thiazolyl)-3-fluorophenoxymethyl]quinoline

Following the procedures described in Example 1, but substituting Phenol 12 for Phenol 1, the title compound was obtained as a solid.

$^1$H NMR (300 MHz, (CD$_3$)$_2$CO): δ5.59 (s, 2H), 7.05 (m, 2H), 7.38 (d, 1H), 7.57 (s, 1H), 7.70 (d, 1H), 7.88–7.99 (m, 4H), 8.25 (s, 1H), 8.33 (s, 1H), 8.42 (d, 1H).

EXAMPLE 14

2-Cyano-4-(3-furyl)-7-[5-(3-pyridyl)-3-fluorophenoxymethyl]quinoline

Following the procedures described in Example 1, but substituting Phenol 13 for Phenol 1, the title compound was obtained as a solid, m.p. 193°–195° C.

EXAMPLE 15

2-Cyano-4-(3-furyl)-7-[5-(2-thienyl)-3-fluorophenoxymethyl]quinoline

Following the procedures described in Example 1, but substituting Phenol 14 for Phenol 1, the title compound was obtained as a solid, m.p. 181°–183° C.

EXAMPLE 16

4-(3furyl)-7-(5-phenyl-3-fluorophenoxymethyl)coumarin

Following the procedures described in Example 2, but substituting Coumarin 1 for Quinoline 1, the title compound was obtained as a solid, m.p. 105°–107° C.

EXAMPLE 17

4-(3-Furyl)-7-(5-phenyl-3-fluorophenylthio)coumarin

A mixture of Coumarin 2 (540 mg), Thiophenol 1 (621 mg) and $K_2CO_3$ (641 mg) in NMP (5 mL) was heated at 120° C. After 3 h, 1N HCl was added and the mixture was extracted with EtOAc. The organics were washed with $H_2O$, brine, dried ($MgSO_4$) and concentrated. Chromatography of the residue (silica gel; hexane/$Et_2O$ (4:1)) provided the title compound as a solid, m.p. 122°–124° C.

EXAMPLE 18

4-Phenyl-7-(5-phenyl-3-fluorophenoxymethyl)coumarin

Following the procedures described in Example 2, but substituting Coumarin 3 for Quinoline 1, the title compound was obtained as a solid, m.p. 129°–131 ° C.

EXAMPLE 19

4-(3-Furyl)-7-(5-phenyl-3-fluorophenylsulfinyl)coumarin

To a solution of 4-(3-furyl)-7-(5-phenyl-3-fluorophenylthio)coumarin (Example 17) (106 mg) in $CHCl_3$ (3 mL) was added m-CPBA (88 mg; 50%). After 2 h, $CH_2Cl_2$ was added and the resulting solution was washed with 10% aq. $NaHSO_3$, saturated aq. $NaHCO_3$, dried ($MgSO_4$) and concentrated. Chromatography of the residue (silica gel; hexane/EtOAc (7:3)) provided the title compound as a solid.

$^1$H NMR (400 MHz, $CDCl_3$): δ6.47 (s, 1H), 6.64 (s, 1H), 7.36–7.48 (m, 5H), 7.54–7.62 (m, 4H), 7.70 (s, 2H), 7.78 (s, 1H), 7.89 (d, 1H).

EXAMPLE 20

4-(3-Furyl)-7-(5-phenyl-3-fluorophenylsulfonyl)coumarin

Following the procedures described in Example 19, but increasing the amount of m-CPBA used to 192 mg from 88 mg, the title compound was obtained as a solid.

$^1$H NMR (400 MHz, $CDCl_3$): δ6.53 (s, 1H), 6.64 (s, 1H), 7.45–7.53 (m, 4H), 7.55 (m, 2H), 7.63 (s, 2H), 7.79 (s, 1H), 7.85 (d, 1H), 7.93 (d, 1H), 7.97 (m, 2H).

EXAMPLE 21

4-(3-Furyl)-7-[5-(3-pyridyl)-3-fluorophenylthio]coumarin

Following the procedures described in Example 17, but substituting Thiophenol 3 for Thiophenol 1, the title compound was obtained as a solid, m.p. 169°–170° C.

EXAMPLE 22

4-(3-Furyl)-7-(6-phenyl-2-pyridylthio)coumarin

Following the procedures described in Example 17, but substituting Coumarin 4 for Coumarin 2 and Pyridine 5 for Thiophenol 1, the title compound was obtained as a solid, m.p. 175°–178° C.

EXAMPLE 23

4-(3-Pyridyl)-7-(5-phenyl-3-fluorophenylthio)coumarin

Following the procedures described in Example 17, but substituting Coumarin 5 for Coumarin 2, the title compound was obtained as a solid.

$^1$H NMR (400 MHz, $CDCl_3$): δ6.34 (s, 1H), 7.10 (d, 1H), 7.20 (m, 2H), 7.25–7.35 (m, 2H), 7.40–7.50 (m, 4H), 7.50–7.55 (m, 3H), 7.80 (s, 1H), 8.71 (s, 1H), 8.80 (d, 1H).

EXAMPLE 24

4-(3-Furyl)-7-[5-(4-fluorophenyl)-3-fluorophenylthio]coumarin

Following the procedures described in Example 17, but substituting Thiophenol 2 for Thiophenol 1, the title compound was obtained as a solid.

$^1$H NMR (400 MHz, $CDCl_3$): δ6.36 (s, 1H), 6.65 (s, 1H), 7.11–7.18 (m, 5H), 7.26 (m, 1H), 7.46 (s, 1H), 7.50–7.53 (m, 2H), 7.60 (s, 1H), 7.67 (d, 1H), 7.78 (s, 1H).

EXAMPLE 25

4-(4-Fluorophenyl)-7-(5-phenyl-3-fluorophenylthio)coumarin

Following the procedures described in Example 17, but substituting Coumarin 6 for Coumarin 2, the title compound was obtained as an oil.

$^1$H NMR (400 MHz, $CDCl_3$): δ6.28 (s, 1H), 7.08 (d, 1H), 7.15 (d, 1H), 7.19–7.22 (m, 3H), 7.28–7.50 (m, 7H), 7.50–7.60 (m, 3H).

EXAMPLE 26

4-(3-Pyrrolyl)-7-(5-phenyl-3-fluorophenylthio)coumarin

Following the procedures described in Example 17, but substituting Coumarin 7 for Coumarin 2, the title compound was obtained as an oil.

$^1$H NMR (400 MHz, $CDCl_3$): δ6.32 (s, 1H), 6.50 (t, 1H), 6.93 (t, 1H), 7.10–7.20 (m, 4H), 7.20–7.30 (m, 3H), 7.34–7.46 (m, 4H), 8.00 (d, 1H), 8.60–8.70 (br s, 1H).

EXAMPLE 27

4-(4-Oxazolyl)-7-[5-(4-fluorophenyl)-3-fluorophenylthio]coumarin

Following the procedures described in Example 24, but substituting Coumarin 8 for Coumarin 2, the title compound was obtained as a solid.

$^1$H NMR (400 MHz, $CDCl_3$): δ6.65 (s, 1H), 7.10–7.30 (m, 6H), 7.45–7.50 (m, 3H), 7.65 (s, 1H), 7.85 (d, 1H), 8.10 (s, 1H).

EXAMPLE 28

4-(3-Pyridyl)-7-[5-(4-fluorophenyl)-3-fluorophenylthio]coumarin

Following the procedures described in Example 23, but substituting Thiophenol 2 for Thiophenol 1, the title compound was obtained as a solid.

$^1$H NMR (400 MHz, CDCl$_3$): δ6.21 (s, 1H), 7.07–7.16 (m, 4H), 7.18 (s, 1H), 7.24–7.30 (m, 2H), 7.42–7.52 (m, 4H), 7.65 (d, 1H), 8.70 (s, 1H), 8.76 (d, 1H).

EXAMPLE 29

2-Cyano-4-(3-furyl)-7-(6-phenyl-2-picolyloxy)naphthalene

A mixture of Pyridine 1 (80 mg), 2-cyano-4-(3-furyl)-7-hydroxy naphthalene (WO 94/00444, 111 mg), triphenylphosphine (146 mg) and di-t-butylazodicarboxylate (128 mg) in THF (7 mL) was stirred at r.t. for 4 h. The mixture was concentrated and the residue chromatographed (silica gel; hexane/EtOAc (5:1)) to provide the title compound as a solid, m.p. 131°–133° C.

EXAMPLE 30

2-Cyano-4-(3-furyl)-7-[6-(4-chlorophenyl)-2-picolyloxy]naphthalene

Following the procedures described in Example 29, but substituting Pyridine 2 for Pyridine 1, the title compound was obtained as a solid, m.p. 174°–177° C.

EXAMPLE 31

2-Cyano-4-(3-furyl)-7-[6-(4-fluorophenyl)-2-picolyloxy]naphthalene

Following the procedures described in Example 29, but substituting Pyridine 3 for Pyridine 1, the title compound was obtained as a solid, m.p. 168°–170° C.

EXAMPLE 32

2-Cyano-4-(3-furyl)-7-(5-phenyl-3-picolyloxy)naphthalene

Following the procedures described in Example 29, but substituting Pyridine 4 for Pyridine 1, the title compound was obtained as a solid, m.p. 138°–140° C.

EXAMPLE 33

2-Cyano4-(3-furyl)-7-(6-phenyl-2-pyridylthio)naphthalene

A mixture of Pyridine 5 (117 mg), Naphthalene 1 (125 mg) and K$_2$CO$_3$ (138 mg) in NMP (6 mL) was heated at 100°–110° C. After 3 h, the mixture was cooled to r.t. and saturated NH$_4$C$_1$ and H$_2$O were added. The mixture was extracted with EtOAc and the organics were washed with H$_2$O, dried (MgSO$_4$), and concentrated. Chromatography of the residue (silica gel; hexane/ethyl acetate (5:1)) provided the title compound as a solid after trituration with Et$_2$O-hexane, m.p. 143°–146° C.

EXAMPLE 34

4-Phenyl-7-[5-(4-fluorophenyl)-3-fluorophenylthio]isoquinoline

A mixture of Thiophenol 2 (50 mg), Isoquinoline 1 (61 mg), tetrakis (triphenylphosphine) palladium (11 mg) and potassium t-butoxide (0.24 mL of a 1M THF solution) in 1-butanol (4 mL) was heated at 105° C. for 90 min. H$_2$O was added and the mixture was extracted with EtOAc. The organics were washed with brine, dried (MgSO$_4$) and concentrated. Chromatography (silica gel; toluene/EtOAc (10:1)) provided the title compound as a foam.

$^1$H NMR (400 MHz, (CD$_3$)$_2$CO): δ7.10 (d, 1H), 7.19 (t, 2H), 7.35 (d, 1H), 7.48–7.59 (m, 6H), 7.67–7.75 (m, 2H), 7.90 (d, 1H), 8.28 (s, 1H), 8.46 (s, 1H), 9.27 (s, 1H).

What is claimed is:

1. A compound of Formula I:

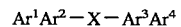

wherein:

Ar$^1$ is Ph—(R$^1$)$_2$, Py, Fu, Th or Tz;

Ar$^2$ is Phe-(R$^2$)$_2$, or Pye;

Ar$^3$ is 2H-1-benzopyran-2-one;

Ar$^4$ is Ph—(R$^1$)$_2$, Py, Fu, Ox, or Pyr;

X is OCH$_2$, CH$_2$O, S, S(O), or S(O)$_2$;

R$^1$ is H, lower alkyl, lower alkoxy, lower alkylthio, lower alkylsulfinyl, lower alkylsulfonyl, CN, CF$_3$, CO$_2$R$^4$, or halogen;

R$^2$ is H, lower alkyl, lower alkoxy, lower alkylthio, CN, CF$_3$ or halogen; and R$^4$ is H or lower alkyl.

2. A compound of claim 1 wherein

Ar$^1$ is Ph, F—Ph or Py;

Ar$^2$ is F-Phe, or Pye;

Ar$^4$ is Ph, F—Ph, Py, Fu, Ox, or Pyr; and

X is OCH$_2$, S, S(O), or S(O)$_2$.

3. A pharmaceutical composition comprising a therapeutically effective amount of a compound of claim 1 and a pharmaceutically acceptable carrier.

4. The pharmaceutical composition of claim 3 additionally comprising an effective amount of a second active ingredient selected from the group consisting of non-steroidal anti-inflammatory drugs; peripheral analgesic agents; cyclooxygenase inhibitors; leukotriene antagonists; leukotriene biosynthesis inhibitors; H$_1$- or H$_2$-receptor antagonists; antihistaminic agents; prostaglandin antagonists; and ACE agonists.

5. A pharmaceutical composition according to claim 4, wherein the second active ingredient is a non-steroidal anti-inflammatory drug.

6. A pharmaceutical composition comprising a therapeutically effective amount of a compound of claim 1, an effective amount of a second active ingredient which is a non-steroidal anti-inflammatory drug, and a pharmaceutically acceptable carrier, wherein the weight ratio of said compound of claim 1 to said second active ingredient ranges from about 1000:1 to 1:1000.

7. A method of preventing the synthesis, the action, or the release of SRS-A or leukotrienes in a mammal which comprises administering to said mammal an effective amount of a compound of claim 1.

8. The method of claim 7 wherein the mammal is man.

9. A method of treating asthma in a mammal comprising administering to a mammal in need of such treatment a therapeutically effective amount of a compound of claim 1.

10. A method of treating inflammatory diseases of the eye in a mammal which comprises administering to a mammal in need of such treatment a therapeutically effective amount of a compound of claim 1.

11. The method of claim 10 wherein the mammal is man.

12. A compound of claim 1 selected from the group consisting of:

4-(3-furyl)-7-(5-phenyl-3-fluorophenoxymethyl)coumarin;

4-(3-furyl)-7-(5-phenyl-3-fluorophenylthio)coumarin;

4-phenyl-7-(5-phenyl-3-fluorophenoxymethyl)coumarin;

4-(3-furyl)-7-(5-phenyl-3-fluorophenylsulfinyl)coumarin;

4-(3-furyl)-7-(5-phenyl-3-fluorophenylsulfonyl)coumarin;

4-(3-furyl)-7-[5-(3-pyridyl)-3-fluorophenylthio]coumarin;

4-(3-furyl-7-(6-phenyl-2-pyridylthio)coumarin;

4-(3-pyridyl)-7-(5-phenyl-3-fluorophenylthio)coumarin;

4-(3-furyl)-7-[5-(4-fluorophenyl)-3-fluorophenylthio]coumarin;

4-(4-fluorophenyl)-7-(5-phenyl-3-fluorophenylthio)coumarin;

4-(3-pyrrolyl)-7-(5-phenyl-3-fluorophenylthio)coumarin;

4-(4-oxazolyl)-7-[5-(4-fluorophenyl)-3-fluorophenylthio]coumarin; and 4-(3-pyridyl)-7-[5-(4-fluorophenyl)-3-fluorophenylthio]coumarin.

* * * * *